United States Patent [19]
Welsh et al.

[11] Patent Number: 5,962,429
[45] Date of Patent: Oct. 5, 1999

[54] COMPLEXES OF ADENOVIRUS WITH CATIONIC MOLECULES

[75] Inventors: Michael J. Welsh, Riverside; Allen J. Fasbender, Solon, both of Iowa

[73] Assignee: University of Iowa, Iowa City, Iowa

[21] Appl. No.: 08/755,035

[22] Filed: Nov. 22, 1996

[51] Int. Cl.[6] .................................................. A61K 48/00
[52] U.S. Cl. ..................... 514/44; 424/93.2; 424/93.6; 435/455; 435/456
[58] Field of Search .............................. 514/44; 424/93.2, 424/93.6; 435/320.1, 235.1, 455, 456

[56] References Cited

U.S. PATENT DOCUMENTS

| | | | |
|---|---|---|---|
| 5,552,309 | 9/1996 | March | 435/172.3 |
| 5,670,488 | 9/1997 | Gregory et al. | 514/44 |
| 5,798,250 | 8/1998 | Zeytinoglu | 435/235.1 |

FOREIGN PATENT DOCUMENTS

| | | |
|---|---|---|
| WO9521259 | 8/1995 | WIPO . |
| WO9603977 | 2/1996 | WIPO . |
| WO9618372 | 6/1996 | WIPO . |
| WO9622765 | 8/1996 | WIPO . |

OTHER PUBLICATIONS

Singh et al. Nucleic Acids Research. vol. 24, No. 15, pp. 3113–3114, 1996.
Vogt, P.K. Virology. vol. 33, No. 1, pp. 175–177, 1967 abstract only.
Farhood et al. Ann. N. Y. Acad. Sci. pp. 23–35, 1994.
Curiel, D., et al., PNAS, vol. 88, pp. 8850–8854, 1991.
Rosenfeld, M., et al., Cell, vol. 68, pp. 143–155, 1992.
Orkin, S., et al., 1995, Report to the NIH Director, 1995.
Douglas et al. (1996) *Nature Biotechnology* 14:1574.
Ellison et al. (1996) *J. Mol. Cell. Cardiol.* 28:1385.
Wickham et al. (1996) *Nature Biotechnology* 14:1570.
Zabner et al. (1995) *J. Biol. Chem.* 270:18997.

*Primary Examiner*—James Ketter
*Assistant Examiner*—Irem Yucel
*Attorney, Agent, or Firm*—Baker Botts

[57] ABSTRACT

The present invention provides noncovalent complexes of cationic molecules and adenoviral vectors containing a transgene. The complexes of the invention exhibit increased efficiency of gene transfer to a target cell relative to adenoviral vectors alone. Methods of making and using the complexes are also provided. A method of delivering cystic fibrosis transmembrane conductance regulator to a CF patient utilizing a complex of cationic molecules and adenoviral vectors containing a transgene encoding a CFTR protein is provided.

17 Claims, 18 Drawing Sheets

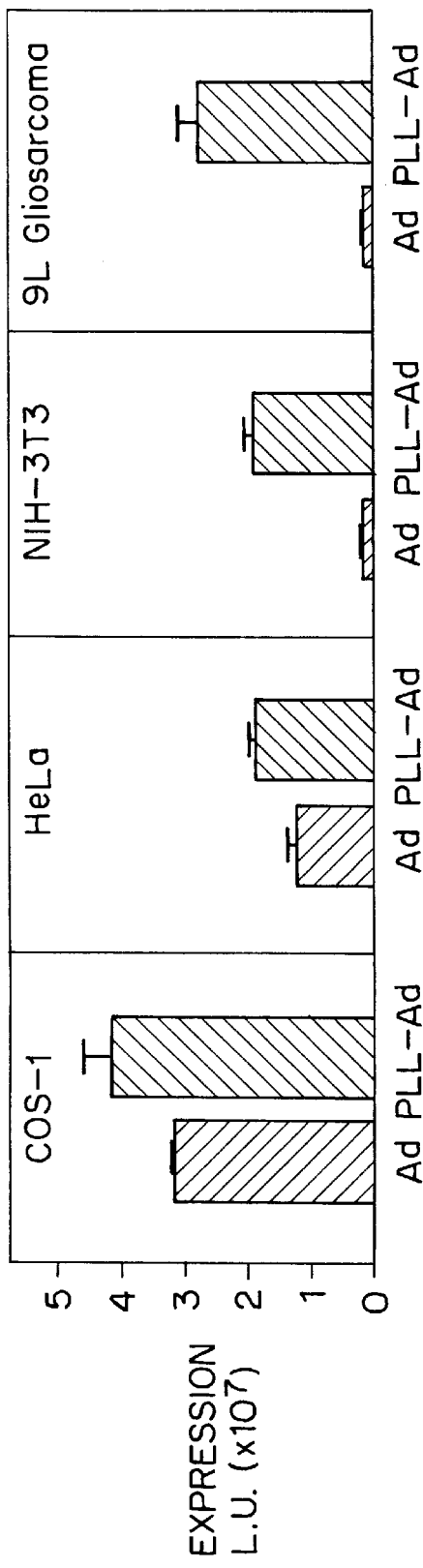
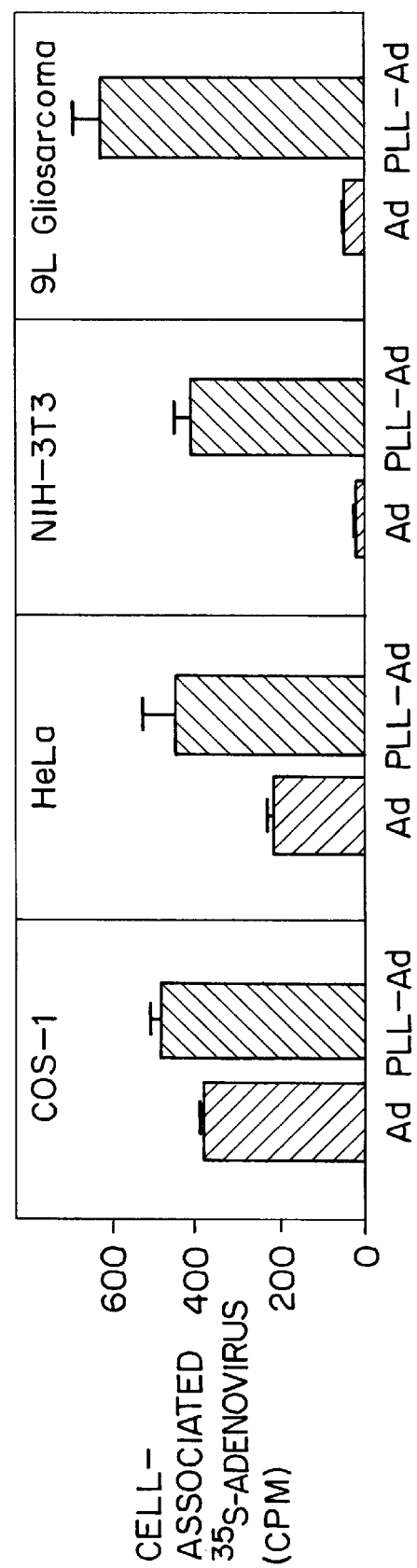
FIG. 1A
FIG. 1B

COMPLEXES OF ADENOVIRUS WITH CATIONIC MOLECULES

FIELD OF THE INVENTION

This invention was made with government support under HL51670 and HL42385 awarded by the National Heart, Lung and Blood Institute of the National Institutes of Health. The government has certain rights in the invention.

The effective use of transgenes for the treatment of inherited and acquired disorders requires efficient delivery of the transgenes. The present invention provides noncovalent complexes of cationic molecules and adenoviral vectors containing transgenes. The complexes of the invention exhibit increased efficiency of gene transfer relative to adenovirus alone, particularly in cells that are poorly infected by adenovirus.

BACKGROUND OF THE INVENTION

Effective use of transgenes for the treatment of inherited and acquired disorders requires efficient delivery of transgenes. Various vector systems have been developed that are capable of delivering a transgene to a target cell. However, there remains a need to improve efficiency of available gene transfer methods. Improved efficiency is desirable both to increase the ability of the vector to correct the cellular defect, and to decrease the required amount of the vector and thereby reduce toxicity.

Transfer of the cystic fibrosis transmembrane conductance regulator (CFTR) cDNA to airway epithelia of patients with cystic fibrosis (CF) provides an example of the successful use of gene transfer to correct a cellular defect, i.e., the CF defect in electrolyte transport. Vector systems including adenoviral vectors (Zabner et al. (1993) *Cell* 75: 207; Knowles et al. (1995) *New Engl. J. Med.* 333: 823; Hay et al. (1995) *Hum. Gene. Ther.* 6: 1487; and Zabner et al. (1996) *J. Clin. Invest.* 97: 1504) and cationic lipids (Caplen et al. (1995) *Nat. Med.* 1: 39) are capable of transferring the CFTR cDNA and expressing CFTR in mature ciliated human airway epithelia. The successful delivery of CFTR in such cells is manifest in a functional chloride ion channel in the treated cells Currently used adenoviral vectors are less than optimal in delivering the CFTR cDNA to airway epithelia because the binding of the virus to the apical surface of the epithelium is limited. Grubb et al. (1994) *Nature* 371: 802. The limited infection can be partially overcome by increasing the contact time between the virus and the apical surface. Zabner et al. (1996) *J. Virol.* 70: 6994.

Cationic lipid vector-mediated gene transfer to mature human airway epithelia is also suboptimal. Caplen et al. (1995) *Nat. Med.* 1: 39. While it appears that cationic molecules bind to the cell surface and in some cases are taken up by the cell, important barriers to transgene expression may be release of DNA from the endosome, entry into the nucleus, release of DNA from the cationic molecule, and transcription of the DNA. Zabner et al. (1995) *J. Biol. Chem.* 270: 18997.

Gene transfer systems that combine viral and nonviral components have been reported. Cristiano et al. (1993) *Proc. Natl. Acad. Sci. USA* 90: 11548; Wu et al. (1994) *J. Biol. Chem.* 269: 11542; Wagner et al. (1992) *Proc. Natl. Acad. Sci. USA* 89: 6099; Yoshimura et al. (1993) *J. Biol. Chem.* 268: 2300; Curiel et al. (1991) *Proc. Natl. Acad. Sci USA* 88: 8850; Kupfer et al. (1994) *Hum. Gene Ther.* 5: 1437; and Gottschalk et al. (1994) *Gene Ther.* 1: 185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes. Further, the transferred gene is contained in plasmid DNA that is exogenous to the adenovirus. In these formulations, large amounts of adenovirus are required, and the increases in gene transfer are often modest.

Accordingly, there is a need in the art for improved vector systems for the efficient delivery of transgenes to target cells. The present invention overcomes the limitations associated with adenoviral vectors and cationic lipid vectors while retaining the desirable features of each vector system.

SUMMARY OF THE INVENTION

The present invention provides noncovalent complexes of cationic molecules and adenoviral vectors in which the adenoviral vectors contain a transgene. In a preferred embodiment, the cationic molecule is a cationic polymer, a cationic lipid, a cationic sugar, a cationic protein, or a cationic dendrimer. Pharmaceutical compositions comprising the complexes of the invention and a pharmaceutically acceptable carrier are also provided.

In another embodiment, the present invention is directed to a method of making a complex of cationic molecules and adenoviral vectors containing a transgene comprising mixing the cationic molecules with the adenoviral vectors. In a preferred embodiment cationic molecules and adenoviral vectors are combined at a ratio at which gene transfer by the complex to a host cell is optimal.

In another embodiment, the present invention provides a method of delivering a transgene to a cell. The method of delivering the transgene to a cell comprises preparing a complex of cationic molecules and adenoviral vectors containing the transgene, and introducing the complex into a cell. In a preferred embodiment, the complex is introduced into the cell by infection.

The present invention also provides a method of introducing a transgene encoding a cystic fibrosis transmembrane conductance regulator (CFTR) protein into the cells of a cystic fibrosis (CF) patient. The method comprises preparing a complex of cationic molecules and adenoviral vectors containing a transgene encoding a CFTR protein, and contacting said complex with the cells of a CF patient. In a preferred embodiment the cells are airway epithelial cells.

In another embodiment, a method of providing CFTR to the airway epithelial cells of a CF patient is provided. The method comprises administering a therapeutically effective amount of a complex comprising cationic molecules and adenoviral vectors containing a transgene encoding a CFTR protein to the airway epithelial cells of a CF patient.

BRIEF DESCRIPTION OF THE DRAWINGS

FIG. 1A depicts β-galactosidase expression in COS-1, HeLa, NIH-3T3 and 9L gliosarcoma cells infected with $^{35}$S-labeled adenovirus alone (Ad) or complexed with poly-L-lysine (PLL-Ad).

FIG. 1B depicts virus uptake in COS-1 HeLa, NIH-3T3 and 9L gliosarcoma cells infected with $^{35}$S-labeled adenovirus alone (Ad) or complexed with poly-L-lysine (PLL-Ad).

DETAILED DESCRIPTION OF THE INVENTION

Figure 2A:
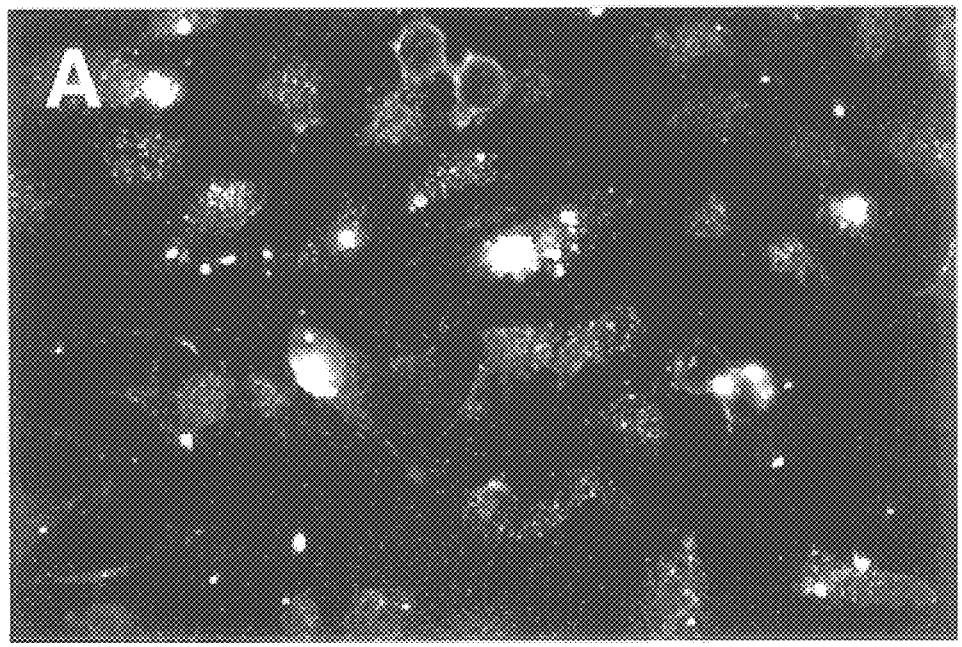
FIGS. 2A–D show Cy3-labeled PLL bound to the surface of COS-1 (FIG. 2A), HeLa (FIG. 2B), NIH-3T3 (FIG. 2C) and 9L gliosarcoma (FIG. 2D) cell lines. The scale bar indicates 25 μm.

The present invention provides complexes of cationic molecules and adenoviral vectors that are useful for the delivery of a transgene to a cell. These complexes are capable of binding and uptake by a target cell. The complexes are particularly useful for adenovirus-mediated gene transfer to cells that are not easily infected by adenovirus alone, for example cells that do not express a cell surface receptor that binds adenovirus fiber. The adenovirus fiber molecules are found on the surface of adenovirus and are believed, inter alia, to mediate viral infectivity.

In addition, the present complexes are useful for delivering an adenovirus vector to a specific cell type. In the complexes of the present invention in which the cationic molecule masks part of the adenovirus, in particular the adenovirus fiber, the specificity of the adenovirus for its widely distributed natural targets may be reduced or eliminated. Since the present complexes retain infectivity despite masking of the fiber, the complex can be delivered to a desired target for effective transgene delivery. In addition, a targeting molecule can be linked to the cationic component of the complex in order to deliver the complex to a specific cell type.

A further advantage of the complexes of the present invention relates to inactivation of adenovirus by neutralizing antibodies. The presence of neutralizing antibodies currently limits the possibility of repeat administration of adenovirus of the same serotype. In complexes of the present invention in which the cationic molecule coats or encapsulates the adenovirus, binding and inactivation by neutralizing antibodies is minimized or prevented. Thus the present complexes provide an improved vehicle for delivery to cells of a transgene contained in an adenoviral vector.

In the complexes of the present invention, the adenoviral vector maintains its ability to facilitate delivery of a transgene. Transfer of a transgene to cells that are not well infected by adenovirus alone is enhanced by the present complexes.

The cationic molecule component of the complex of the present invention is a cationic molecule that enhances gene transfer by an adenoviral vector to a cell type in which infection by adenovirus alone is limited. Poorly infected cells include, for example, NIH-3T3 and 9L gliosarcoma cells, which are useful as in vitro model systems for assays of the complexes of the invention. Other cells that are poorly infected by adenovirus, such as human endothelial cells, readily express a transgene product when treated with the complexes of the present invention. A simple and convenient assay to determine the ability of a cationic molecule to enhance gene transfer is provided hereinbelow.

Cationic molecules are known to those of ordinary skill in the art. In a preferred embodiment, the cationic molecule is a cationic polymer, a cationic lipid, a cationic sugar, a cationic protein, or a cationic dendrimer. The cationic molecules may be combined with non-cationic molecules. Cationic polymers include, for example, poly-L-lysine (PLL), polyethyleneimine (PEI), DEAE-dextran, and histone (fraction V-S), and cationic dendrimers. Those of ordinary skill in the art can determine the molecular weight of the cationic polymer that provides optimal gene transfer in accordance with the methods described herein. For example, PLL is preferably used at a average molecular weight of 55.8 kDa, corresponding to about 250 lysine residues. PEI is preferably used at an average molecular weight of 25 kDa. In a preferred embodiment the cationic polymer is PLL.

Cationic lipids are known to those of ordinary skill in the art. Representative cationic lipids include those disclosed e.g., by U.S. Pat. No. 5,283,185 and PCT/US95/16174 (WO96/18372), the disclosures of which are incorporated herein by reference. In a preferred embodiment the cationic lipid is (N-($N^1$,$N^1$-dimethylaminoethane) carbamoyl] cholesterol (DC-Chol) disclosed in U.S. Pat. No. 5,283,165. In another preferred embodiment, the cationic lipid is $N^4$-spermine cholesterol carbamate (GL-67) or $N^4$-spermidine cholesterol carbamate (GL-53) disclosed in WO96/18372. Other representative cationic lipids include (2, 3-dioleyloxy-N-[2(sperminecarboxamido)ethyl]-N,N-dimethyl-1-propanaminium trifluoroacetate (DOSPA), dioctadecylamidoglycyl spermine (DOGS), commercially available as TRANSFECTAM® from Promega, Madison, Wis.; 1,3-dioleoyloxy-2-(6-carboxyspermyl)-propyl amide (DOSPER); N-[1-(2,3-Dioleoyloxy)propyl]-N,N,N-trimethyl-ammoniummethylsulfate (DOTAP); N-[1-2(2,3-dioleyloxy)propyl]-N,N,N-trimethylammonium chloride (DOTMA); (±)-N-(2-Hydroxyethyl)-N,N-dimethyl-2,3-bis (tetradecyloxy)-1-propanaminium bromide (DMRIE); (±)-N-(2-Aminoethyl)-N,N-dimethyl-2,3-bis (tetradecyloxy)-1-propanaminium bromide (βAE-DMRIE); dimethyldioctadecylammonium bromide (DDAB); LIPOFECTIN®, a 1:1 (w/w) formulation of DOTMA and dioleoyl phosphotidylethanolamine (DOPE) commercially available from Life Technolgies, Gaithersburg, Md.; LIPOFECTAMINE®, a 3:1 (w/w) formulation of DOSPA and DOPE commercially available from Life Technologies, Gaithersburg, Md.; LIPOFECTACE™, a 1:2.5 (w/w) formulation of DDAB and DOPE, commercially available from Life Technologies, Gaithersburg, Md.; Tfx™ -50, a reagent consisting of N,N,N', N'-tetramethyl-N-N'-bis(2-hydroxyethyl)-2,3,-dioleoyloxy-1, 4-butanediammonium iodide and DOPE, commercially available from Promega, Madison, Wis.; and DMRIE-C™, a 1:1 (molar ratio) formulation of DMRIE and cholesterol commercially available from Life Technologies, Gaithersburg, Md. In a preferred embodiment the cationic lipid is GL-53 or GL-67. In accordance with the present invention, the cationic lipid may be combined with a colipid such as DOPE or cholesterol.

The adenoviral vector component of the complex of the present invention contains adenoviral DNA and a transgene of interest. The transgene is operably linked to a promoter and regulatory sequences to effect expression of the transgene in the target cell.

Adenovirus-based vectors for the delivery of transgenes are well known in the art and may be obtained commercially or constructed by standard molecular biological methods. Recombinant adenoviral vectors containing exogenous genes for transfer are generally derived from adenovirus type 2 (Ad2) and adenovirus type 5 (Ad5). They may also be derived from other non-oncogenic serotypes. See, e.g., Horowitz, *Adenoviridae and Their Replication*, in Viroloqy, Second Edit., Fields, et al, Eds., Raven Press Ltd., New York, 1990, incorporated herein by reference.

The adenoviral vectors in the present invention are incapable of replicating, have minimal viral gene expression and are capable of expressing the transgene in target cells. Adenoviral vectors are generally made replication-defective by deletion of the E1 region genes. The replication-defective vectors may be produced in the 293 cell (ATCC CRL 1573), a human embryonic kidney cell line expressing E1 functions. The deleted E1 region may be replaced by the transgene of interest under the control of an adenoviral or non-adenoviral promoter. The transgene may also be placed in other regions of the adenovirus genome. Graham et al. "Adenovirus-based expression vectors and recombinant vaccines" in *Vaccines: New Approaches to Immunological Problems*, 363–390, Ellis, ed., Butteworth-Heinemann, Boston, 1992 provide a review of the production of replication-defective adenoviral vectors, and is incorporated herein by reference.

The skilled artisan is also aware that other non-essential regions of the adenovirus can be deleted or repositioned within the viral genome to provide an adenoviral vector suitable for delivery of a transgene in accordance with the present invention. For example, PCT/US93/11667 (WO94/12649), the disclosure of which is incorporated herein by reference, discloses that some or all of the E1 and E3 regions may be deleted, and non-essential open reading frames of E4 can be deleted. Other representative adenoviral vectors are disclosed, for example by Rich et al. (1993) *Human Gene Therapy* 4: 461, Brody et al (1994), *Ann NY Acad Sci.* 716: 90, Wilson (1996) *New Engl. J. Med.* 334: 1185, Crystal (1995) *Science* 270: 404; O'Neal et al. (1994) *Hum. Mol. Genet.* 3: 1497; and Graham et al. (1992) in "Vaccines: New Approaches to Immunologic Problems", Butterworth-Heinemann, Boston, 363–390, the disclosures of which are incorporated herein by reference. In a preferred embodiment of the present invention, the adenoviral vector is an E1 deleted Ad2- or Ad5-based vector.

A transgene is defined herein as any nucleic acid or gene that is not native to adenovirus. Any nucleic acid that can be transcribed in the adenoviral vector is contemplated. In a preferred embodiment, the transgene encodes a biologically functional protein or peptide. A biologically functional protein or peptide is a protein or peptide that affects the cellular mechanism of a cell in which it is expressed, or the function of a tissue or an organism. For example, the biologically functional protein or peptide may be essential for normal growth or repair of a cell, for maintaining the health of an organism, or for producing a secreted protein that acts at a site distant from the cell or tissue in which it was produced. The protein or peptide may maintain or improve the health of a mammal by supplying a missing protein, by providing increased quantities of a protein that is under-produced, or by providing a protein or peptide that inhibits or counteracts an undesired molecule. Transgenes that express a biologically functional protein or peptide useful in the prevention or treatment of an inherited or acquired disorder in a mammal are particularly preferred. Examples of such biologically functional proteins include cytokines, growth factors, tumor suppressors, and clotting factors.

In one embodiment of the present invention, the transgene is DNA encoding functional cystic fibrosis transmembrane conductance regulator (CFTR) protein. CFTR is a phosphorylation and nucleoside triphosphate-regulated $Cl^-$ channel located in the apical membrane of epithelial cells in the lung, intestine, pancreas and sweat glands. For a review, see Welsh et al., (1992) *Neuron* 8: 821, incorporated herein by reference. Cystic fibrosis (CF) results from a non-functional $Cl^-$ channel in an individual's epithelial cells caused by mutations in the gene encoding CFTR. Such mutations result in loss of function of the chloride channel and thus defective electrolyte transport in affected epithelial cells. DNA encoding wild-type CFTR is known in the art; the sequence is disclosed, for example, in PCT US93/11667 (WO94/12649) incorporated herein by reference. A deletion mutant of CFTR that encodes a regulated $Cl^-$ channel is disclosed by Sheppard et al. (1994) *Cell* 76: 1091, and in PCT/US95/03680 (WO95/25796), the disclosures of which are incorporated herein by reference.

In accordance with the present invention, DNA encoding a CFTR protein includes the foregoing published sequences as well as other DNA encoding CFTR known to those of skill in the art. Further included are modifications of the known DNA molecules, for example mutations, substitutions, deletions, insertions and homologs, that encode a functional CFTR protein, i.e., a chloride channel.

DNA encoding a CFTR protein can be identified by those of ordinary skill in the art by its ability, upon expression in host cells, to correct the Cl$^-$ channel defect in cultured CF airway epithelia, for example by the methods described by Rich et al. (1990) *Nature* 347: 358, incorporated herein by reference. Briefly, cultured CF airway epithelial cells are infected with adenoviral vectors containing DNA encoding a CFTR protein. Virus-mediated expression of functional CFTR protein is assessed using an SPQ [6-methoxy-N-(3-sulfopropyl)-quinolinium, Molecular Probes, Eugene, Org.] halide efflux assay. SPQ is a halide-sensitive fluorophore, the fluorescence of which is quenched by halides. In this assay, cells are loaded with SPQ, CFTR is activated by cAMP agonists, the CFTR Cl$^-$ channel opens, halides exit the cell, and SPQ florescence in the cell increases rapidly. Thus increases in intracellular fluorescence in response to cAMP provide a measure of a functional Cl$^-$ channel.

In another assay suitable to identify functional CFTR proteins, CF epithelial cells are infected with adenoviral vectors containing DNA encoding a CFTR protein, and secretion of Cl$^-$ from infected cells is measured in response to cAMP stimulation. The secretion of Cl$^-$ can be measured as an increase in transepithelial short-circuit current with addition of cAMP agonists, as described for example by Rich et al. (1993) *Human Gene Therapy* 4: 461, the disclosure of which is incorporated herein by reference. Expression of a functional CFTR protein can also be assessed by patch clamp techniques that detect reversibly activated whole-cell currents in response to addition of cAMP agonists, or single-channel currents in excised, cell-free patches of membrane in response to cAMP-dependent protein kinase and ATP. Patch clamp techniques are described for example by Sheppard et al. (1994) *Cell* 76: 1091.

In another embodiment, the transgene is a nucleic acid that is capable of being transcribed into an RNA molecule that is sufficiently complementary to hybridize to an mRNA or DNA of interest. Such an RNA molecule is referred to herein as an antisense molecule. Antisense molecules are useful in preventing or limiting the expression of overproduced, defective, or otherwise undesirable nucleic acid molecules.

In the adenoviral vectors of the present invention, the transgene is operably linked to expression control sequences, e.g., a promoter that directs expression of the transgene. The promoter may be an endogenous adenovirus promoter, for example the E1a promoter or the Ad2 major late promoter (MLP) or a heterologous eucaryotic promoter, for example a phosphoglycerate kinase (PGK) promoter or a cytomegalovirus (CMV) promoter. Similarly, those of ordinary skill in the art can construct adenoviral vectors utilizing endogenous or heterologous poly A addition signals.

In accordance with the present invention, the noncovalent complexes are formed by combining adenoviral vectors containing a transgene with cationic molecules, for example by mixing. The vectors and cationic molecules may be diluted with a pharmaceutically acceptable carrier or diluent, for example, a physiological buffer, such as saline, phosphate buffered saline (PBS), water, dextrose, and solutions with pharmaceutical excipients such as polyethylene glycol (PEG), propylene glycol and glycerol. For complexes that are intended to be assayed in cultured cells, for example to determine optimal ratios of cationic molecules to adenoviral vector, cell culture medium is used to dilute the vectors and cationic molecules. Those of ordinary skill in the art appreciate that the choice of a diluent is dictated by the intended use of the complex, and can choose an appropriate diluent in accordance with known formulation principles. The complexes of the present invention are preferably prepared in the absence of serum. After the complex is formed, it may be used in the presence or absence of serum.

The adenoviral vectors containing a transgene and the cationic molecules are preferably combined at a ratio that achieves optimal transfer of the transgene to a target cell. The ratio may be conveniently determined by utilizing a reporter gene as the transgene, preparing complexes of varying ratios of adenoviral vector to cationic molecules, and infecting target cells with the complexes. Transfer of the transgene to the target cell is evaluated by measuring the level of the transgene product in the target cell. The level of transgene product in the host cell directly correlates with the efficiency of transfer of the transgene by the complex. Expression of the transgene can be monitored by a variety of methods including, inter alia, immunological, histochemical and activity assays, depending upon the selected transgene. For example, if the transgene encodes β-galactosidase, activity can be measured by methods well known in the art, for example by using a commercially available method such as a Galacto-Lite kit (Tropix, Inc., Bedford, Mass.) as disclosed by Zabner et al. (1996) *Gene Therapy* 3: 458. When the transgene is DNA encoding a CFTR protein, the presence of a functional regulated chloride channel in host cells can be determined by the methods disclosed by Sheppard et al. (1994) *Cell* 1: 1091 and PCT/US95/03680 (WO95/25796), incorporated herein by reference. The foregoing assay for optimizing ratios is also useful for identifying cationic molecules that maximize transgene delivery.

Thus, by measuring the expression of the transgene transferred by complexes comprising varying ratios, a suitable ratio of cationic molecules to adenoviral vectors can be determined. The ratios herein are described in terms of the average number of cationic molecules per adenoviral particle. The useful ratios of cationic molecules per adenoviral particle vary depending upon the choice of a cationic molecule. For example, it has been found in accordance with the present invention that for complexes containing PLL having an average size of 55.8 kDa, a suitable ratio is from about 50 to about 1000 molecules of PLL per adenovirus particle. The following ratios of cationic molecule per adenoviral particle achieved efficient gene transfer: histone (fraction V-S), 5000; PEI, 500; DEAE-dextran, 25,000; DC-Chol/DOPE, $2.6\times10^6$; DC-Chol, $1.7\times10^7$; GL-53/DOPE, $2\times10^5$; GL-53, $9.2\times10^5$; GL-67/DOPE, $1\times10^6$; GL-67, $8.7\times10^5$; DMRIE/DOPE, $1.6\times10^6$; βAE-DMRIE, $1.7\times10^7$; Tfx-50, $3\times10^5$; DOGS, $1.7\times10^5$; LIPOFECTAMINE™ (DOSPA/DOPE), $6.9\times10^4$. These ratios can be optimized by those of ordinary skill in the art in accordance with the teachings herein. The cationic molecules and adenoviral vectors are diluted and then mixed at the selected ratio in the absence of serum to form the complexes of the invention. The complexes are then used to transfer a transgene to a cultured cell or to a cell or tissue or organ in vivo. In a preferred embodiment, the complexes are used within about five hours from the time of preparation. In a more preferred embodiment, the complexes are used within from about fifteen minutes to about one hour from the time of preparation. Those skilled in the art can readily determine suitable methods for stabilizing the complexes, for example using excipients such as polyethyleneglycol (PEG).

The complexes of the present invention are useful for transferring a transgene to a target cell. The complexes are particularly useful for the transfer of a transgene to a cell that is not easily infected by adenovirus alone. The target cell may be in vitro or in vivo. Use of the complexes in vitro allows the transfer of a transgene to a cultured cell and is useful for the recombinant production of the transgene product. Use of the complexes to deliver a transgene to a cell in vivo is useful for the treatment of various disorders, for example in which the transgene product is absent, insufficient, or nonfunctional. Alternately, the expression of the transgene may serve to block the expression or function of an undesired gene or gene product in the target cell.

Accordingly, the present invention provides a method of delivering a transgene to a cell. The method comprises combining cationic molecules with adenoviral vectors containing the transgene to form a noncovalent complex, and introducing the complex into a cell. In a preferred embodiment, the cell is one that is not easily infected by adenovirus alone. The complex may be introduced into the cell by methods known in the art, including for example infection. Infection of a target cell in culture is accomplished by incubating the target cell with the complex. Conditions of time, temperature, environment and culture media are standard conditions for infection of cultured cells and are within the skill of those in the art. For example, representative conditions for the infection of cultured airway epithelial cells are infection with 5,000 to 10,000 viral particles/cell, for fifteen minutes to six hours in a 5% $CO_2$ humidified environment at 37° C. Effective delivery of the transgene to the target cell can be confirmed by detecting the transgene product as described above.

Infection of a target cell in vivo is accomplished by contacting the target cell with the complex. The complex is delivered as a pharmaceutical composition in combination with a pharmaceutically acceptable carrier. As used herein, the term "pharmaceutically acceptable carrier" includes any and all solvents, diluents, isotonic agents, and the like. The use of such media and agents for pharmaceutical compositions is well known in the art. The complexes of the invention may be delivered to the target cell by methods appropriate for the target cell, including for example by ingestion, injection, aerosol, inhalation, and the like. The complexes may be delivered intravenously, by injection into tissue, such as brain or tumor, or by injection into a body cavity such as pleura or peritoneum. In a preferred embodiment, the transgene is a DNA molecule encoding CFTR or an analog or variant thereof which provides functional regulated chloride channel activity in target cells, and the complex is delivered to the airway epithelia by inhalation.

The complexes of the present invention may also be used to target an adenoviral vector containing a transgene to a specific cell type. This targeting may be accomplished by linking a targeting molecule to the cationic component of the complex. A targeting molecule is any agent that is specific for a cell or tissue type of interest, including for example a ligand, antibody, sugar or other receptor binding molecule. The ability of the present complex to target a transgene to a specific cell or tissue renders the present complexes particularly useful in the treatment of cancer, genetic disorders, and acquired disorders.

The present invention further provides a method of delivering a transgene encoding CFTR or variant thereof capable of forming a chloride channel to the cells of a CF patient. The method comprises combining cationic molecules with adenoviral vectors containing the transgene to form a non-covalent complex, and contacting said complex with the cells of CF patient. In a preferred embodiment the cells are airway epithelial cells. The complex may be delivered to the target cells as a pharmaceutical composition comprising the complex and a pharmaceutically acceptable carrier. The complex may be delivered to airway epithelial cells by methods known in the art, for example by inhalation or intubation and lavage. In a preferred embodiment, delivery of the complex is by inhalation.

The present invention further provides a method of providing CFTR to airway epithelial cells of CF patients. The method comprises combining cationic molecules with an adenoviral vector containing a transgene encoding CFTR to form a noncovalent complex and administering a therapeutically effective amount of the complex to epithelial cells of a CF patient in a fashion and under conditions whereby functional $Cl^-$ channel activity is produced in the treated cells. As used herein the term "therapeutically effective amount" refers to an amount that alleviates the chloride channel defect by the production of functional $Cl^-$ channels in the defective epithelia of a CF patient. Production of functional $Cl^-$ channels in CF patients can be evaluated by the alleviation of the symptoms associated with CF such as abnormal mucous secretion, bacterial infection, inflammation, tissue damage and fibrosis. The term "transgene encoding CFTR" includes DNA molecules that encode a $Cl^-$ channel that, when expressed in an airway epithelial cells of a CF patient, alleviate the chloride channel defect in the airway epithelial cells. In a preferred embodiment, the transgene has the sequence disclosed in PCT US93/11667 or PCT US95/03680, the disclosures of which are incorporated herein by reference. The complex may be administered to the epithelial cells as a pharmaceutical composition comprising the complex and a pharmaceutically acceptable carrier. The complex may be administered by medically acceptable routes for delivery to epithelial cells. In a preferred embodiment the cells are airway epithelial cells and the complex is delivered by inhalation or intubation and lavage. For example, the composition may be administered to nasal epithelium using a modified Foley catheter, which is introduced under endoscopic guidance to the area beneath the inferior turbinate as described by Zabner et al. (1996) *J. Clin. Invest.* 6: 1504. In tubation and lavage is described by Welsh et al. (1995) *Human Gene Therapy* 6: 205. In a preferred method, the composition comprises the complex and phosphate buffered saline or other carrier and is administered by inhalation of aerosol, dry powder, or by instillation, for example by bronchoscopy.

The present invention further provides pharmaceutical compositions comprising noncovalent complexes of cationic molecules and adenoviral vectors containing a transgene and further comprising a pharmaceutically acceptable carrier. In a preferred embodiment the cationic molecule is a cationic polymer or a cationic lipid. In another preferred embodiment the transgene encodes CFTR.

The formulation of pharmaceutical compositions is generally known in the art and reference can conveniently be made to Remington's Pharmaceutical Sciences, 17th ed., Mack Publishing Co., Easton, Pa. The pharmaceutical forms of the present complexes suitable for administration include sterile aqueous solutions and dispersions. The subject complexes are compounded for convenient and effective administration in pharmaceutically effective amounts with a suitable pharmaceutically acceptable carrier and/or diluent in a therapeutically effective dose.

The precise therapeutically effective amount of complex to be used in the methods of this invention applied to humans can be determined by the ordinary skilled artisan with consideration of individual differences in age, weight, extent of disease and condition of the patient. It can generally be stated that the pharmaceutical preparation of the present invention should be preferably administered in an amount of at least about 1 plaque forming unit (PFU) per desired target cell.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The specification for the novel dosage unit forms of the invention are dictated by and directly depend on the unique characteristics of the complex and the limitations inherent in the art of compounding.

The principal active ingredient is compounded for convenient and effective administration in effective amounts with a suitable pharmaceutically acceptable carrier in dosage unit form as hereinabove disclosed. In the case of compositions containing supplementary active ingredients, the dosages are determined by reference to the usual dose and manner of administration of the ingredients.

In the method of treatment according to the present invention, the complexes may be administered in a manner compatible with the dosage formulation, in such amount as will be therapeutically effective, and in any way which is medically acceptable for the treatment of CF.

The invention is further illustrated by the following specific examples which are not intended in any way to limit the scope of the invention.

EXAMPLE 1

Materials and Methods

COS-1, NIH-3T3, and 9L gliosarcoma (Weizsaecker et al. (1981) *J. Neurol*. 244: 183) cells were cultured on 24-well plates (Corning, 25820) in Dulbecco's modified Eagle's medium (DMEM) (high glucose) supplemented with 10% fetal calf serum (FCS) (Sigma Chemical Co., St. Louis) and 100 U/ml penicillin and 100 μg/ml streptomycin (P/S). HeLa cells were cultured on 24-well plates in Eagle's minimal essential medium (MEM) supplemented with 10% FCS, 10 mM nonessential amino acids (Sigma) and P/S. All cells were seeded at $3 \times 10^4/cm^2$ except for 9L gliosarcoma cells which were seeded at $7.5 \times 10^4/cm^2$. Primary cultures of human umbilical vein endothelial cells (HUVEC) were cultured in M199 media (Gibco) supplemented with P/S, 1% L-glutamine, and Basal Medium Eagle Vitamin Solution (Gibco), and Basal Medium Eagle Amino Acids (Gibco) as described by Jaffe et al. (1973) *J. Clin. Invest*. 52: 2745. HUVEC cells were seeded at $1 \times 10^5/cm^2$ 18–24 hours prior to infection. Primary cultures of rat heptocytes were isolated as described by Berry and Friend (1969) *J. Cell Biol*. 43: 506. The isolated cells were placed in culture medium consisting of Eagles MEM 75% and Waymouth's 25% supplemented with 10% FCS, 2 mM L-glutamine, 4 μg/ml dexamethasome (Sigma), 10 ng/ml triiodothyronine (Sigma), 50 ng/ml epidermal growth factor (Sigma) and ITS Universal Culture Supplement (Collaborative Biomedical Products) and seeded onto collagen-coated 24-well plates at $4 \times 10^5$ cells/cm² or on collagen-coated 96-well plates at 7500 cells/well. Primary cultures of normal and CF human airway epithelia (HAE) were grown on permeable filter supports at the air-liquid interface as described by Smith et al. (1996) *Cell* 85: 229.

The recombinant adenoviral vectors expressing β-galactosidase, Ad2/βGal-2, or Ad5RSVLacZ, and CFTR, Ad2/CFTR-8, were prepared as follows. Ad2/βGal-2 and Ad2/CFTR-8 are derived from the vector Ad2/CFTR-2 described by Armentano et al. (1995) *Human Gene Therapy* 6: 1353 and disclosed in allowed U.S. patent application Ser. No. 08/136,742 both of which are incorporated herein by reference. Ad2/CFTR-2 is an adenovirus 2-based E1 replacement vector. The vector is derived from a full length (37.5 kb) copy of the Ad2 genome from which the early region 1 (E1) genes are deleted and replaced by a CFTR expression cassette with the CFTR cDNA (nucleotides 123–4622 of the published CFTR sequence), the phosphoglycerate kinase (PGK) promoter, and a synthetic bovine growth hormone polyadenylation site. The vector retains the E3 region but lacks all of E4 with the exception of ORF6.

In Ad2/βGal-2, the CFTR expression cassette is replaced by a DNA fragment containing the cytomegalovirus (CMV) promoter and the β-galactosidase coding sequence with a 5' nuclear-localization signal from the SV40 T antigen.

In Ad2/CFTR-8, the E1 region deletion was extended from nucleotide 3328 to 4019 to delete the pIX coding sequences. The pIX promoter and coding sequences (nucleotides 3519 to 4061) were cloned downstream from the ORF6 cDNA. An SV40 polyadenylation signal sequence was cloned into a position between the ORF6 and pIX sequences. The pIX gene in this vector is transcribed in a left to right direction. The CFTR expression cassette in Ad2/CFTR-8 differs from Ad2/CFTR-2 in that the promoter is the A2 E1a promoter, and the SV40 polyadenylation signal sequence is used. The relocation of the pIX gene in Ad2/CFTR-8, the construction and use of which are disclosed in U.S. patent application Ser. No. 08/409,874, filed Mar. 24, 1995, incorporated herein by reference, greatly reduces the production of recombinant competent adenovirus (RCA) during propagation of the vector. Ad5RSVLacZ was constructed as described by Davidson et al. (1994) *Experimental Neurology* 125: 258.

Wild-type 2 adenovirus was provided by Dr. Sam Wadsworth at Genzyme, Framingham, Mass. In some examples adenovirus was labeled by production in the human embryonal kidney cell line 293 (ATCC CRL 1573) in methionine-free medium containing 1 mCi/100 μl of $^{35}$S-methionine (American Life Science, Arlington Heights, Ill.). Fiber protein was a gift of Dr. Paul Freimuth (Brookhaven National Laboratories, Upton, N.Y.).

Various size poly-L-lysine hydrobromide (PLL) polymers were obtained from Sigma Chemical Co. (St. Louis, Mo). Poly-L-lysine of 55.8 kDa average molecular weight (corresponding to approximately 250 lysine resides) was used in all examples unless otherwise noted. Polyethyleneimine (PEI), average molecular weight of 25,000, was obtained from Aldrich Chemical Co. Histone (fraction V-S) and spermine were obtained from Sigma Chemical Co. (St. Louis, Mo.). Lipofectin, Lipofectace, and Lipofectamine were obtained from Gibco BRL (Gaithersburgh, Md.). DEAE-Dextran, and dioctadecylamidoglycyl spermine (DOGS) were obtained from Promega (Madison, Wis.).

The lipids $N^{4+}$spermine cholesteryl carbamate (GL-67), $N^{4+}$spermidine cholesteryl carbamate (GL-53), and [N-(N', N'-dimethylaminoethane)carbamoyl]cholesterol (DC-Chol) were gifts from Drs. Seng Cheng and David Harris (Genzyme Corp. Framingham, Mass.). These lipids are disclosed in PCT application PCT/US95/16174 and U.S.

Pat. No. 5,283,185, incorporated herein by reference. In some cases these were formulated in a 1:2 molar ratio of GL-67 to dioleoylphosphatidylethanolamine (DOPE), a 1:1 molar ratio of GL-53 to DOPE, or a 1:2 molar ratio of DC-Chol to DOPE. DOPE was purchased from Avanti Polar Lipids (Alabaster, Ala.). 1,2-dimyristyloxypropyl-3-dimethyl-hydroxyethylammonium bromide (DMRIE) :DOPE at a 1:1 molar ratio and βAE-DMRIE were gifts from Dr. Phil Felgner (Vical Inc. San Diego, Calif.).

Fluorescently-labeled PLL was produced by stirring 2 mg PLL with 400 μl of Flurolink Cy3 (Amersham Life Science, Arlington Heights, Ill.) in 20 mM HEPES pH 7.4 for 30–60 minutes with protection from light. The Cy3-labeled PLL was purified on a PD-10 Sephadex G-25 M desalting column eluted with 20 mM HEPES pH 7.4 (Pharmacia Biotech, Uppsale, Sweden).

Recombinant adenovirus was prepared by the University of Iowa Gene Transfer Vector Core at titers of approximately $1 \times 10^{10}$ I.U./ml. Complexes between cationic components and adenovirus particles were formed by prediluting the cationic component and the adenoviral components in Eagle's MEM (Gibco) in 12×75 mm polystyrene tubes (Fisher, Pittsburgh, Pa.). Ratios of cationic molecules to adenoviral particles and volumes of the dilutions are described below and in individual figure legends. The cationic component dilution was added to the viral particle dilution, mixed by inversion or gentle pipette tip aspiration and allowed to incubate for 15–30 minutes at room temperature before application to cells or tissue. Cationic molecules: adenovirus complexes are described based on calculated average number of cationic molecules per adenovirus.

Cultured cells were infected 18–24 hours after seeding when the cells were approximately 70% confluent. Airway epithelial cells were allowed to mature in culture at the air-liquid interface for at least 10–14 days before use so that they develop a ciliated apical surface that resembles the in vivo airway surface. To the apical surface 50 μl of a Eagle's MEM containing $1.1 \times 10^9$ particles of adenovirus complexed with cationic component at the indicated ratio of cationic molecules per particle was applied. Cultured cells were infected for 10 minutes to 6 hours (times indicated in figure legends) in a 5% $CO_2$ humidified environment at 37° C., the infection solution removed, and fresh serum-containing media added. Cells were then incubated for an additional 24 hours unless otherwise specified. In examples in which uptake of $^{35}S$-labeled adenovirus was assessed, cells were harvested for the measurement of cell-associated radiolabeled virus at the end of the infection period, while paired groups of cells were incubated for an additional 24 hours (unless otherwise noted) and harvested for assessment of gene expression. Human airway epithelial cells were infected as described in individual figure legends.

For gene transfer to the nasal epithelium, Ad2/CFTR-8 was applied to the nasal epithelium of unanesthetized ΔF/ΔF mice (Zeiher et al. (1995) *J. Clin. Invest.* 96: 2051) as a 5 μl drop containing $5 \times 10^7$ IU/nostril of adenovirus alone or PLL-Ad. The transepithelial electric potential difference (Vt) across the nasal epithelium was measured using techniques similar to those described by Zeiher et al. During measurement of Vt, the nasal mucosa was perfused at a rate of 50 μl/min with a Ringer's solution containing (in mM): 135 NaCl, 2.4 $KH_2PO_2$, 0.6$K_2HPO_4$, 1.2 $CaCl_2$, 1.2 $MgCl_2$, and 10 HEPES (titrated to pH 7.4 with NaOH). Three solutions were used: a) Ringer's solution alone, b) Ringer's solution containing 100 μM amiloride (Merck and Co. Inc., West Point, Pa.), or c) Ringer's solution containing 135 mM sodium gluconate (substituted for NaCl), 10 μm terbutaline, and 100 μM amiloride. Measurements were made after perfusion for 5 minutes.

β-Galactosidase activity was assayed using a Galacto-Lite kit (Tropix, Inc., Bedford, Mass.) and a luminometer (Monolight 2010, analytical Luminescence Laboratory, San Diego, Calif.). Cells were removed from dishes or millicell filters by incubation with 120 μl lysis buffer (100 mM potassium phosphate pH 7.8, 0.02% Triton X-100, and 1 mM dithiothreitol) for 15 min followed by scraping. A 4 μl aliquot from each 24-well plate or millicell was used for each Galacto-Lite assay. Protein was measured using Bio-Rad protein assay reagent (Bio-Rad Laboratories, Hercules, Calif.). Data for β-Galactosidase activity represent total values from all cells in one well or from one millicell. All conditions were performed in triplicate on at least two different occasions. For X-Gal staining for β-galactosidase, cells were washed 24 hours after infection and fixed with 1.8% formaldehyde and 2% glutaraldehyde and then incubated for 16 hours in X-Gal solution. Blue staining nuclei were evaluated by light microscopy. For antihexon staining, airway epithelia cultured on permeable filter supports were studied 30 hours after infection. Cells were fixed with acetone:methanol and stained with a polyclonal-FITC labeled anti-hexon antibody (Chemicon, Temecula, Calif.). Hexon positive cells were counted using low magnification fluorescence photomicrographs of the monolayers. This method allows for detection of infected cells by staining for the most abundant adenovirus protein, hexon, conferring better sensitivity than with reporter genes such as β-galactosidase.

To evaluate cell-associated $^{35}S$-adenovirus, cells were harvested at the end of the infection period. The dishes or millicells were washed four times with phosphate-buffered saline pH 7.4, the lysis buffer (as described above) was applied, the dishes were scraped, and the cell lysate counted in a RACK BETA Model 1209 liquid scintillation counter (LKB Wallac, Gaithersburg, Md.).

To evaluate transepithelial electrolyte transport by human airway epithelia, epithelia were mounted in modified Ussing chambers as described by Zabner et al. (1996) *Gene Ther*. 3: 458, incorporated herein by reference. Short circuit current (Isc) was measured under baseline conditions, and after addition of amiloride (10 μM) and cAMP agonists (10 μM forskolin and 100 μM IBMX).

For fluorescence microscopy, cells were seeded on 8-well slides 18–24 hours before testing. The medium was removed and replaced with 200 μl Eagle's MEM supplemented with 5 ng/μl of Cy3-labeled PLL. After a 10 minute incubation at 37° C., the solution was removed, the cells were washed twice with Eagle's MEM and examined by a Bio-Rad MCR-600 confocal microscope for cell-associated fluorescence.

For transmission electron microscopy, complexes of PLL and adenovirus were formed as follows: $9 \times 10^9$ adenovirus particles were prediluted in 50 μl of Eagles's MEM and combined with 0, 4, 250 or 10,000 PLL molecules/particle (0, 3.3, 208, or 8320 ng, respectively) also in 50 μl of Eagle's MEM. The PLL dilution was added to the virus dilution and mixed by gentle pipette tip aspiration. Complexes of cationic lipids with adenoviral particles were formed in a similar fashion. PLL-adenovirus and cationic lipid-adenovirus complexes were processed for transmission electron microscopy (TEM) using a negative stain technique. Fifteen-μl drops of freshly prepared samples were placed on glow-discharged collodion/carbon-coated 400-mesh copper grids for 3 minutes. The solution was wicked off with filter paper and replaced with 1% aqueous uranyl acetate for 30 seconds. After removal of this solution, grids were allowed to dry and imaged in an Hitachi H-7000 transmission electron microscope.

To evaluate the interaction of adenovirus complexes with cells, complexes of PLL or Lipofectamine with adenovirus were formed as follows: $1.5 \times 10^{11}$ adenovirus particles were prediluted in 150 µl of Eagle's MEM and combined with 250 molecules/particle of PLL (3,460 ng PLL) or 68,150 molecules/particle of 2,3-dioleyloxy-N-[2 (sperminecarboxamido)ethyl]-N,N-dimethyl-1-propanaminium trifluoroacetate (DOSPA) (equivalent to 33 µg Lipofectamine) also prediluted in 150 µl Eagle's MEM. The cationic component was added to the virus dilution and mixed by gentle pipette tip aspiration. To follow the cellular entry of cationic:adenovirus complexes, 9L gliosarcoma cells were infected for 15 minutes at 37° C., then the cells were washed and fixed in 2.5% glutaraldehyde and processed using standard electron microscopic procedures. Briefly, the samples were post-fixed in 1% osmium tetroxide, followed by 2.5% aqueous uranyl acetate, and then dehydrated in a graded series of ethanol washes. Thin sections (70 nm) of the Eponate 12-embedded specimen were placed on 135-mesh hexagonal copper grids and post stained with uranyl acetate and Reynold's lead citrate.

EXAMPLE 2

Gene Transfer with Complexes of PLL and Adenovirus

Transgene expression and virus uptake were assessed in COS-1, HeLa, NIH-3T3 and 9L gliosarcoma cells following infection with $^{35}$S-labeled adenovirus alone or complexed with PLL (PLL-Ad). Cells were incubated under serum-free conditions for 90 minutes at 37° C. with 10,000 particles/cell of $^{35}$S-Ad5RSVLacZ or 10,000 particles/cell of $^{35}$S-Ad5RSVLacZ complexed with 250 molecules of PLL/particle. At the end of the infection period, half the cultures were washed, released from the dishes and the lysates counted for cell-associated adenovirus. The rest of the cultures received fresh media and β-galactosidase expression was measured 24 hours later.

As shown in FIG. 1A, the application of Ad5/RSVLacZ alone to COS-1 and HeLa cells generated high levels of β-galactosidase expression, while under identical conditions NIH-3T3 cells and 9L gliosarcoma cells yielded much lower expression levels. Decreased expression was not due to cell-type specific effects on the Rous sarcoma virus promoter because similar effects were found when Ad2/βGal-2 was used. As noted above, Ad2/βGal-2 contains the cytomegalovirus promoter driving β-galactosidase expression.

FIG. 1 also shows that there was a correlation between the amount of adenovirus alone (i.e. not complexed with a cationic molecule) bound to the different cell types and the level of β-galactosidase expression. There was substantial binding to COS-1 and HeLa cells which showed high levels of transgene expression, whereas there was little binding to NIH-3T3 and 9L gliosarcoma cells which showed little transgene expression. These data suggest that low levels of expression in some cells infected by adenovirus alone may be due to limited vector binding.

Figure 2B:
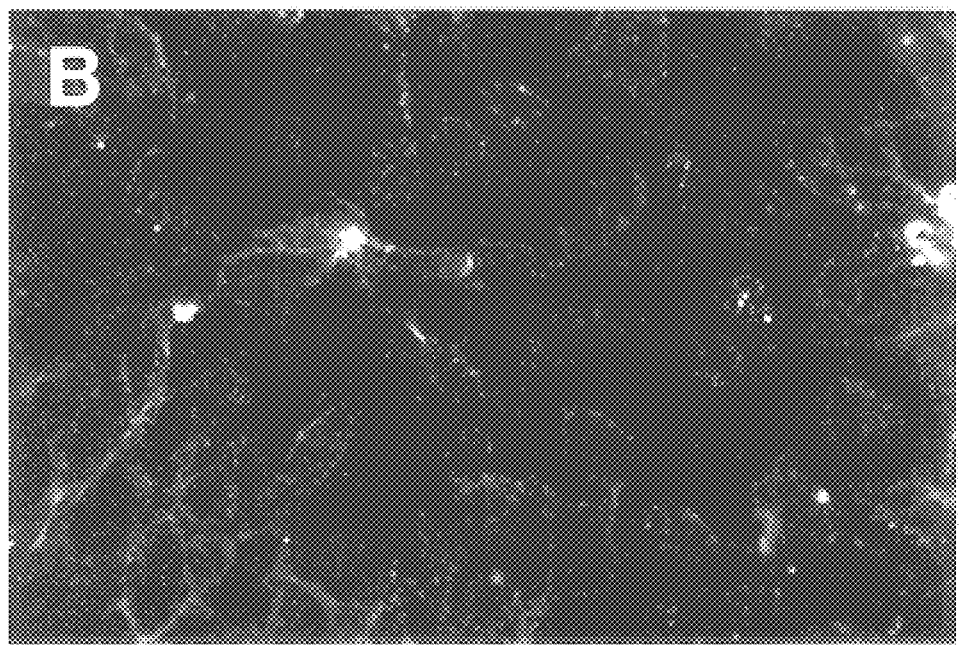
Figure 2C:
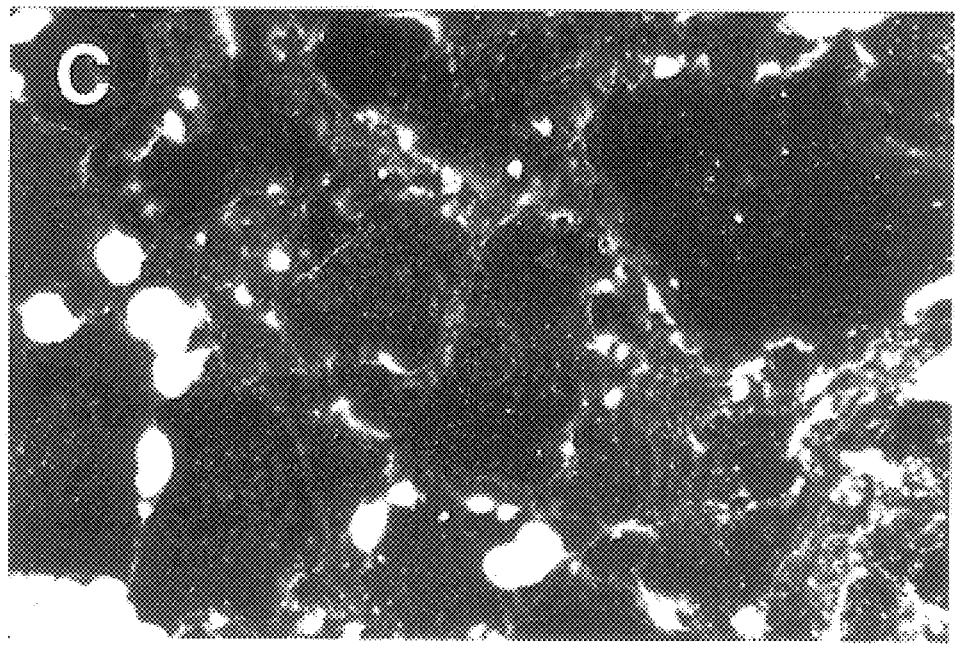
Figure 2D:
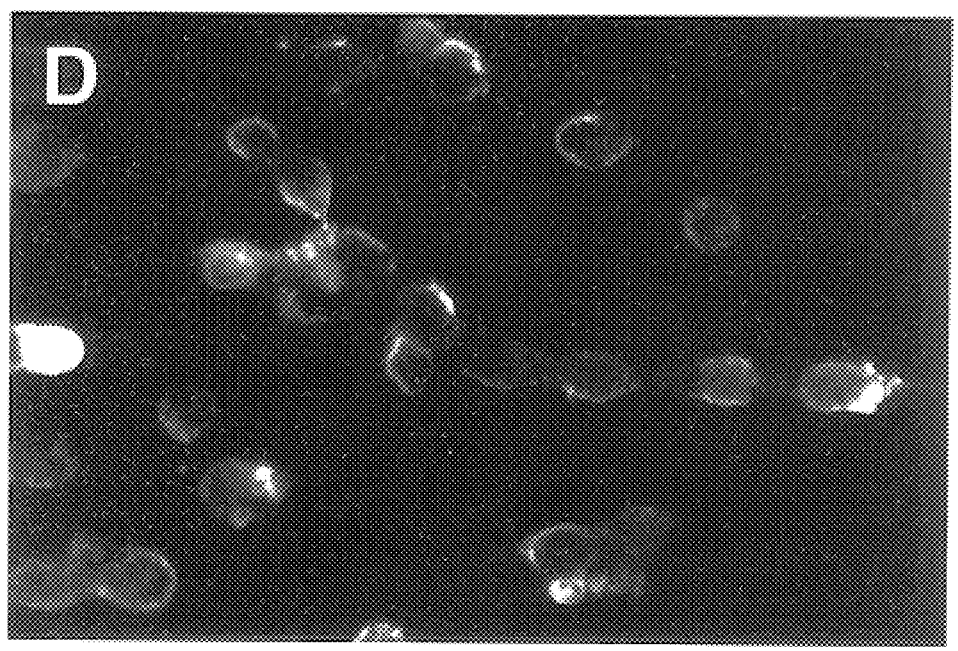
Figure 3A:
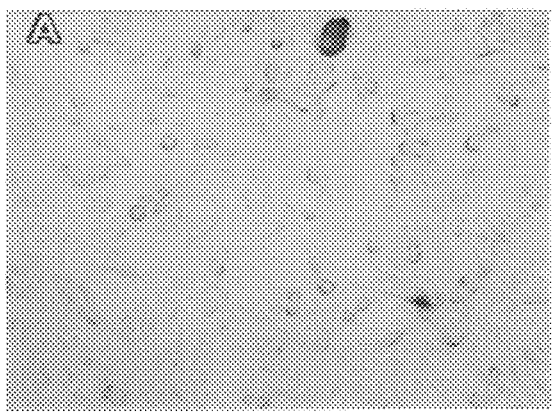
FIGS. 3A–I show X-Gal staining of 9L gliosarcoma (3A, B, C), COS-1 (3D, E, F) and NIH-3T3 (3G, H, I) cells incubated with Ad/βGal-2 (3A, D, G), PLL-Ad/βGal-2 (3B, E, H) and Lipofectamine-Ad/μGal-2 (3C, F, I).
Figure 3D:
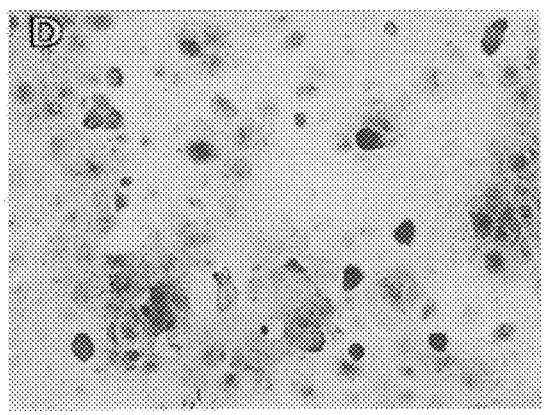
Figure 3B:
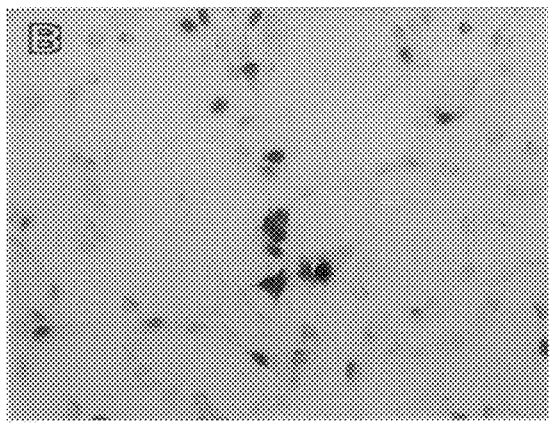
Figure 3E:
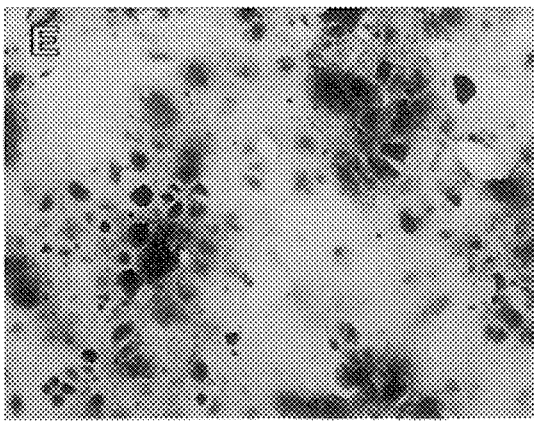
Figure 3C:
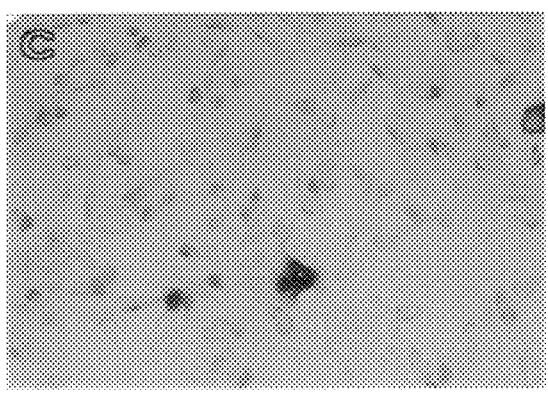
Figure 3F:
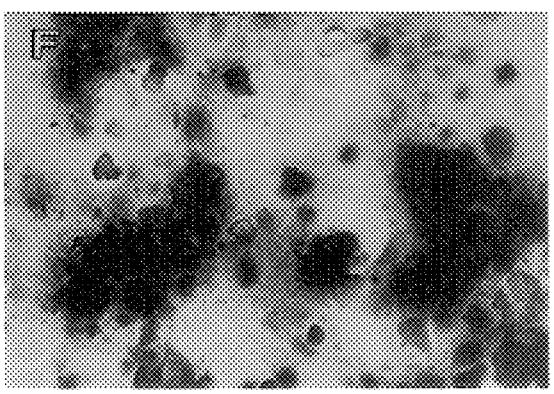
Figure 3G:
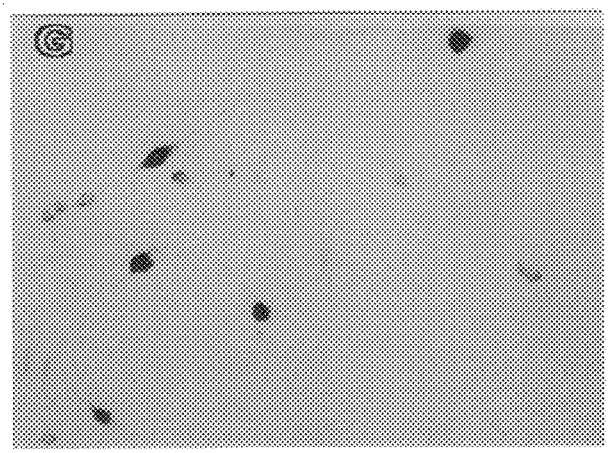
Figure 3H:
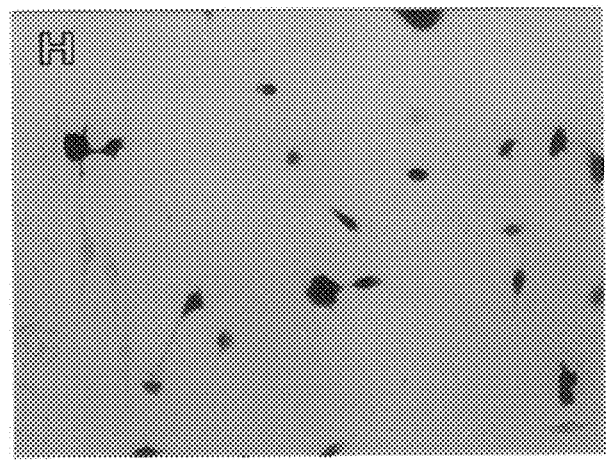
Figure 3I:
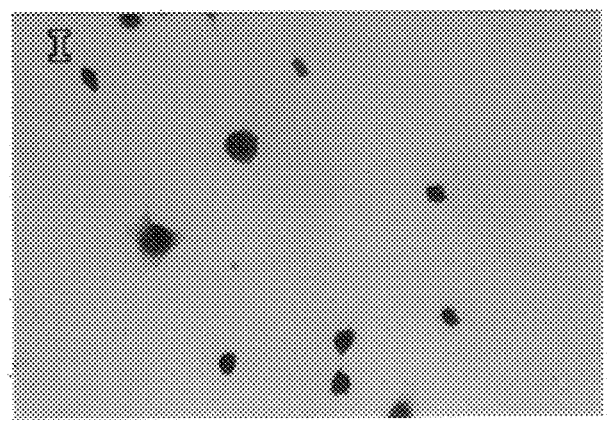

Before applying the PPL-Ad complex to the various cell types, Cy3-labeled PLL was applied to determine whether cationic molecules would bind to the cell surface. Cy3-labeled PLL bound to the surface of the COS-1 (FIG. 2A), HeLa (FIG. 2B), NIH-3T3 (FIG. 2C) and 9L (FIG. 2D) gliosarcoma cell lines. The surface of nearly every cell was fluorescently labeled in all cell types.

FIG. 1 shows that when the PLL-Ad complex was applied to NIH-3T3 and 9L gliosarcoma cells, both adenovirus binding and transgene expression increased into the same range as had been observed with adenovirus alone in COS-1 and HeLa cells. Complexing PLL with adenovirus had small effects on binding and expression in COS-1 and HeLa cells.

FIGS. 3A–I show photomicrographs of 9L gliosarcoma (3A, B, C), COS-1 (3D, E, F) and NIH-3T3 (3G, H, I) cells stained with X-Gal. Cells were incubated with Ad2/βGal-2 (3A, D, G), PLL-Ad (3B, E, H) or Lipofectamine-Ad (Ad2/βGal-2 complexed to Lipofectamine, ~68,000 DOSPA/molecules/particle) (3C, F, I). PLL-Ad not only increased total β-galactosidase activity in NIH-3T3 and 9L gliosarcoma cells, but also increased the number of cells expressing the transgene.

Complexes of PLL-Ad also increased expression in primary cell cultures. In human umbilical vein endothelial cells, which are poorly infected by adenovirus alone, PLL-Ad increased expression 63 ±3-fold(n=3). In contrast, in primary cultures of rat hepatocytes, which are readily infected by adenovirus, PLL-Ad produced little enhancement (PLL-Ad was 1.1.±0.1 the level of expression with adenovirus alone, n=3).

EXAMPLE 3

Gene Transfer with Complexes of Cationic Molecules and Adenovirus

Other cationic molecules were assessed for their ability to enhance gene transfer when noncovalently complexed with adenovirus. Nonlipid cationic polymers (polyethyleneimine (PEI), DEAE-dextran, histone fraction V-S and spermine), cholesterol-based cationic lipids (DC-Chol, GL-53 and G7-67) and noncholesterol type cationic lipids (DMRIE, βAE-DMRIE, Tfx50, DOGS, lipofectamine) were complexed with Ad2/βGal-2 as described in Example 1 over a range of ratios of cationic molecules to adenovirus particle. 9L gliosarcoma cells were incubated with 5000 particles/cell (approximate MOI=50) for 2 hours, the virus solution was then replaced with fresh media, and expression was assessed 24 hours later.

Figure 4:
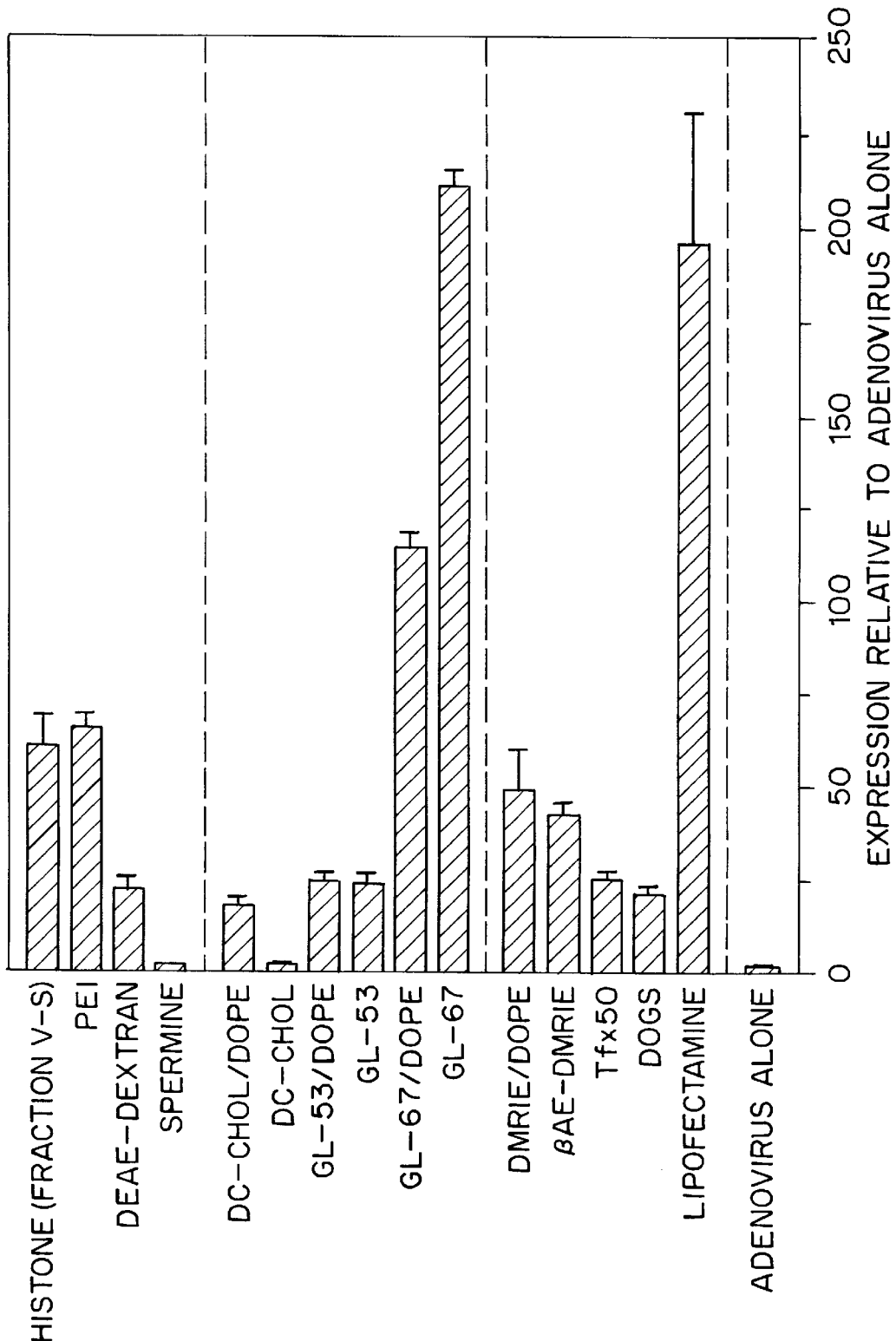
FIG. 4 is a graph of the effect of complexes of adenovirus with various cationic polymers and cationic lipids on expression of a transgene in 9L gliosarcoma cells. Data are β-galactosidase expression relative to expression with adenovirus alone, which was assigned a value of 1.0.

Each cationic molecule was complexed with Ad2/βGal-2 over a range of ratios of cationic molecule to adenovirus particle ratios. The optimum ratio varied with different cationic molecules; data from the optimum ratios are plotted in FIG. 4. The top portion of FIG. 4 shows nonlipid molecules, the middle shows cholesterol-based cationic lipids, and the bottom shows noncholesterol-type cationic lipids. For each cationic substance, the number of cationic molecules/adenoviral particle, and ng per $9 \times 10^9$ particles, respectively, was: histone (fraction V-S), 500, 1620 ng; PEI, 500, 412 ng; DEAE-dextran, 25,000, 9370 ng; spermine, (no optimal ratio was found); DC-Chol/DOPE, $2.6 \times 10^6$, 19,200 ng; DC-Chol, $1.7 \times 10^7$, 128,000 ng; GL-53/DOPE, $2 \times 10^5$, 1760 ng; GL-53, $9.2 \times 10^5$, 8000 ng; GL-67/DOPE, $1 \times 10^6$, 9400 ng; GL-67, $8.7 \times 10^5$, 8000 ng; DMRIE/DOPE, $1.6 \times 10^6$, 15,100 ng; βAE-DMRIE, $1.7 \times 10^7$, 128,000 ng; Tfx-50, $3 \times 10^5$, 4700 ng; DOGS, $1.7 \times 10^5$, 2000 ng; and Lipofectamine, $6.9 \times 10^4$, 1500 ng. n=at least 3 for each molecule. The data shown represent β-galactosidase expression relative to expression with adenovirus alone, which was assigned a value of 1.0.

Polyethyleneimine (PEI), DEAE-dextran, and histone (fraction V-S) all facilitated gene transfer to poorly infected cell types (FIG. 4). With each polymer the optimal cationic molecule/adenoviral particle ratio varied. Spermine (a low molecular weight polyamine with a potential +4 net charge) failed to enhance expression in 9L gliosarcoma cells despite testing of a range of molecule/adenovirus particle ratios (FIG. 4).

Cationic lipids complexed with adenovirus also augmented gene transfer to 9L gliosarcoma cells (FIG. 4). Similar results were obtained in human umbilical vein endothelial cell cultures. It appeared that, in general, polyvalent lipids were more effective than monovalent lipids; e.g. compare DC-Chol(+1 charge), GL-53 (+2 charge), and GL-67(+3 charge). Most DNA/cationic lipid formulations include the neutral lipid DOPE; DOPE is thought to enhance gene transfer because of its fusogenic, endosome-disrupting properties. Inclusion of DOPE in the present complexes, however, did not consistently improve expression, as it usually does with cationic lipid/DNA complexes.

These data indicate that many different cationic molecules can facilitate gene transfer to cells that are normally relatively resistant to adenovirus infection.

EXAMPLE 4

Evaluation of PLL-Adenovirus Complexes

The effect of the ratio of PLL molecules to adenovirus particle on β-galactosidase expression in COS-1, 9L gliosarcoma, and NIH-3T3 cells was examined. Cells were incubated for 2 hours in 500 $\mu$l Eagle's MEM containing 5000 particles/cell (MOI approximately 50) of Ad2/βGal-2 complexed with PLL at the ratio indicated in FIG. 5. Results are graphed in FIG. 5.

Figure 5:
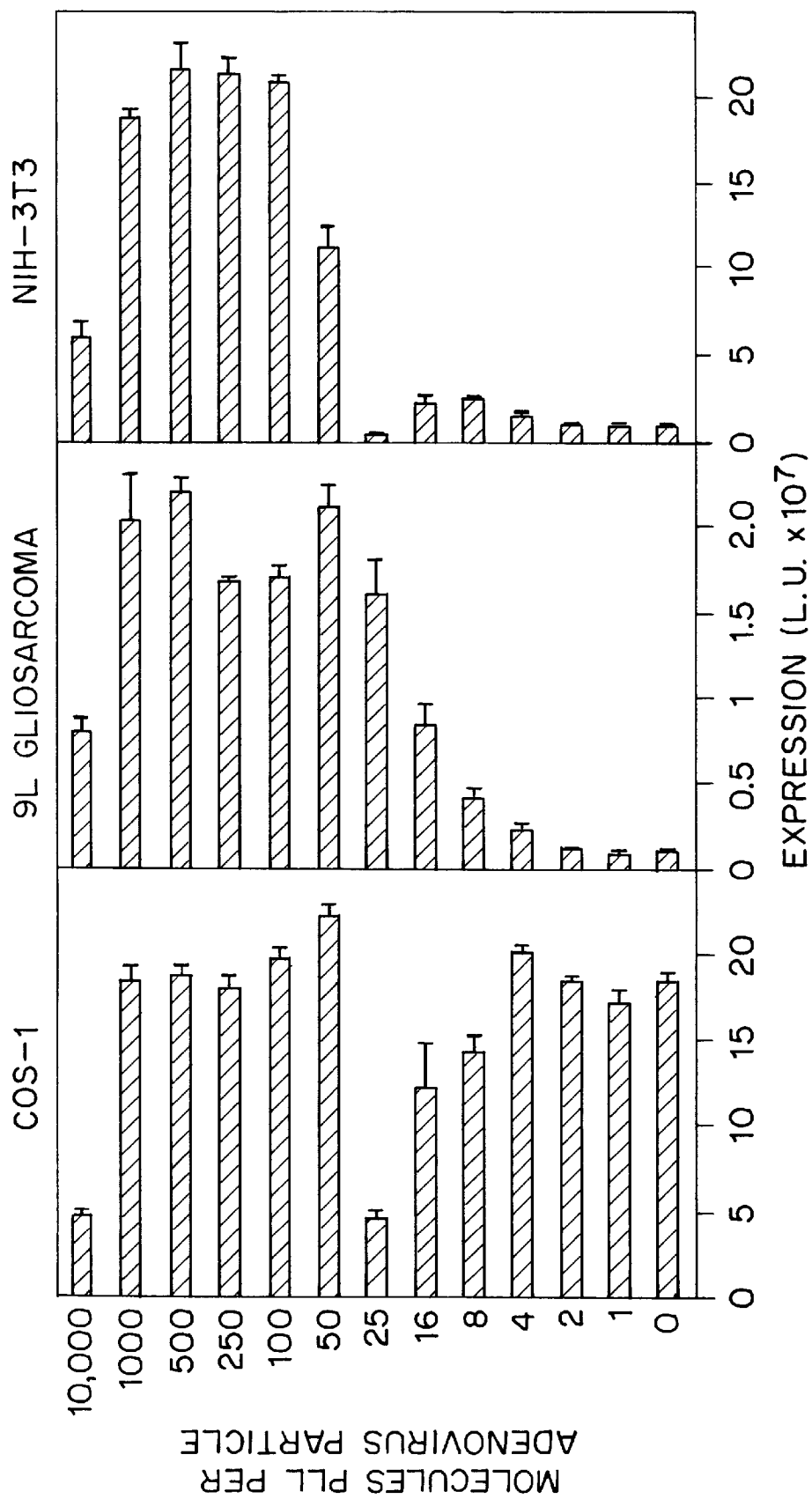
FIG. 5 is a graph depicting the effect of ratio of number of poly-L-lysine (PLL) molecules to adenovirus particles on β-galactosidase expression in COS-1, 9L gliosarcoma and NIH-3T3 cells.
Figure 6A:
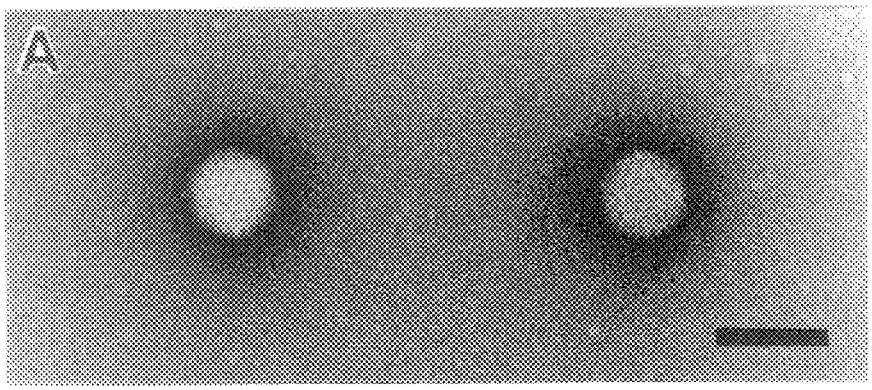
FIGS. 6A–D show electron photomicrographs of adenovirus alone (6A) and PLL-Ad at a ratio of 4 (6B), 250 (6C) and 10,000 (6D) PLL molecules/particle of Ad2/βGal-2. The scale bar indicates 100 nm.
Figure 6B:
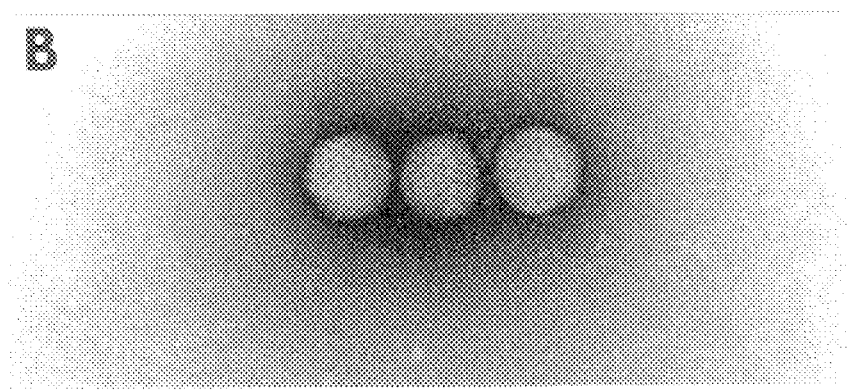
Figure 6C:
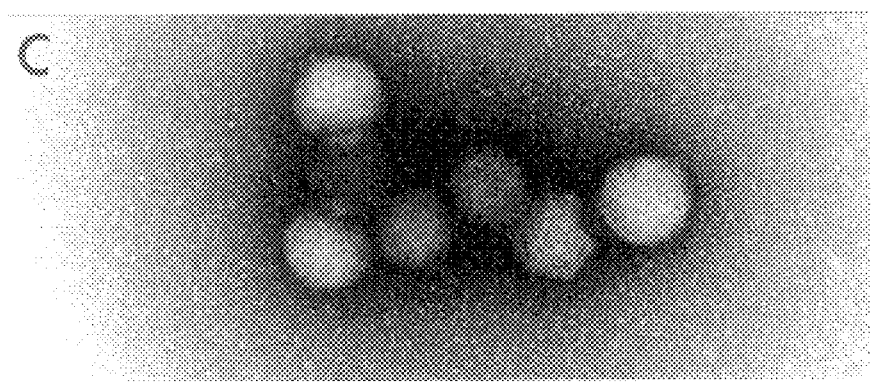
Figure 6D:
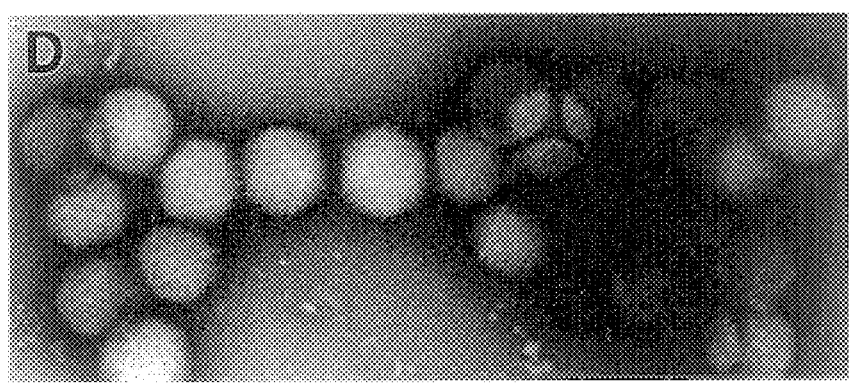

In NIH-3T3 and 9L gliosarcoma cells, as the ratio of PLL to Ad2/βGal-2 increased, the efficiency of gene transfer increased (FIG. 5). Maximum β-galactosidase activity was observed at a ratio of approximately 250 PLL molecules per adenovirus particle. At high ratios of PLL to adenovirus particles, β-galactosidase expression tended to decrease. In contrast, increasing amounts of PLL did not increase β-galactosidase expression by COS-1 cells; in fact at a PLL molecule/particle ratio of about 25, a decrease in expression was frequently noted. These results suggested the possibility that PLL may have interfered with the normal mechanism of adenovirus attachment and infection at intermediate ratios of PLL molecules/adenovirus particle, but as the amount of PLL in the complex was increased, PLL appeared to have mediated adenovirus binding to the cells.

Figure 7:
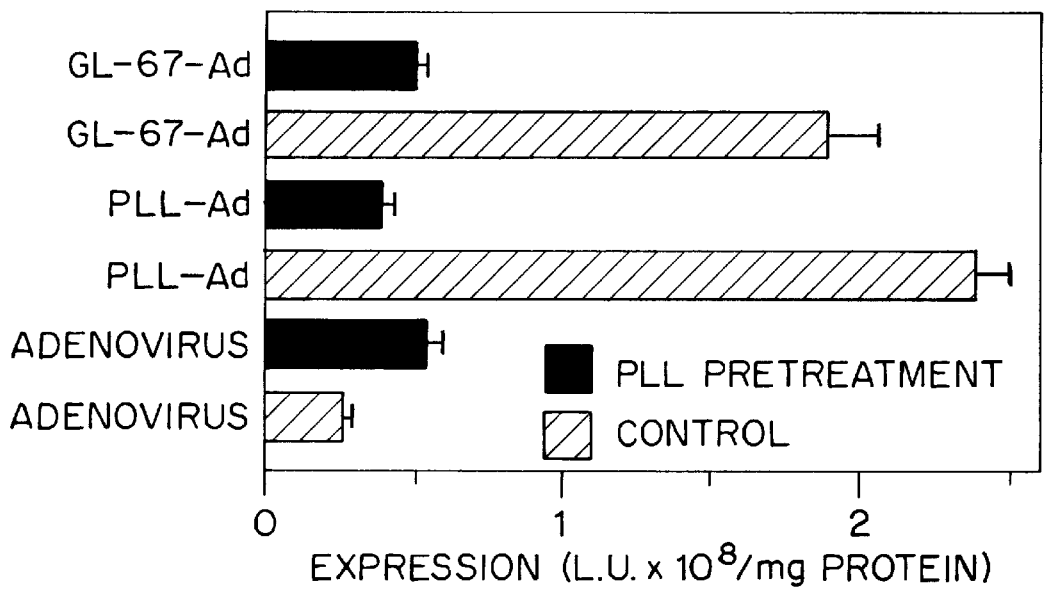
FIG. 7 is a graph depicting the effect of applying PLL to 9L gliosarcoma cells before application of Ad2/βGal-2 or complexes of PLL-Ad or GL-67-Ad.

The effect of applying PLL to 9L gliosarcoma cells before application of Ad2/βGal-2 or complexes of PLL-Ad or GL-67-Ad was determined. Cells were treated for 5 minutes under serum-free conditions with 5 ng/$\mu$l of PLL (FIG. 7, solid bars) or buffer alone (FIG. 7, crosshatched bars). PLL was then removed by rinsing and cells were incubated for 1 hour with 5000 particles/cell of Ad2/βGal-2, PLL-Ad (250 molecules of PLL/particle) or GL-67-Ad ($2.2 \times 10^5$ molecules of GL-67/particle). The virus-containing solution was then replaced with fresh media and the cells were assayed for β-galactosidase activity 24 hours later. Results are shown in FIG. 7. (n=at least 3 for each.)

FIG. 7 shows that separate application of PLL followed by adenovirus was not nearly as effective as adding the preformed PLL-Ad complex to the cells. FIG. 7 also shows that applying PLL to the cells before application of PLL-Ad or GL-67-Ad complexes largely prevented the augmentation of gene transfer observed with these complexes. These results suggest that PLL competed with sites that bind both PLL-Ad and GL-67-Ad, thereby attenuating gene transfer.

The effect of PLL size on gene transfer was examined. Complexes of Ad2/3Gal-2 with PLL of average molecular weight of 8.2, 25.7, 55.8 and 233 kDa were applied to 9L gliosarcoma cells. The ratio of calculated positive charge to adenovirus particle was maintained constant at about $1.2 \times 10^5$. Adenovirus alone or the various PLL-Ad complexes were applied to cells at 5000 particles/cell for 1 hour, the cells were washed, and β-galactosidase activity was measured 24 hours later.

Figure 8A:
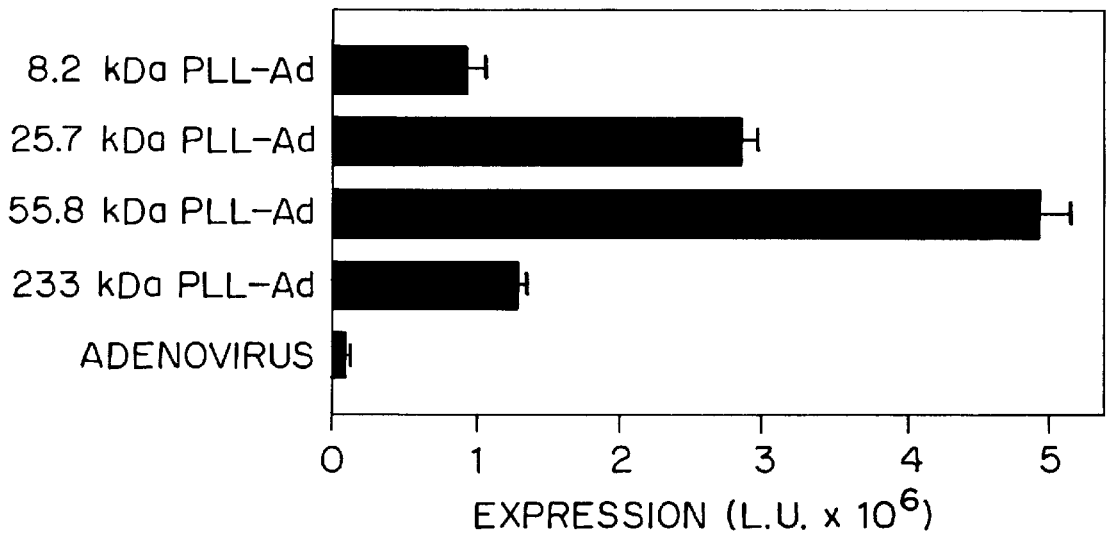
FIG. 8A is a graph depicting the effect of PLL size on gene transfer mediated by complexes of Ad2/βGal-2 and PLL in 9L gliosarcoma cells.

As shown in FIG. 8A, the size of PLL influenced gene transfer. A size of 55.8 kDA (used throughout the preceding examples) produced the greatest augmentation of gene transfer when compared to PLL of other sizes, even though the calculated ratio of positive charges/adenovirus particle remained constant. Many cationic lipid:DNA complexes have a tendency to aggregate and lose their effectiveness with prolonged incubation (Gao et al. (1996) *Biochemistry* 35: 1027). A similar property was observed with PLL-Ad. With a 5 hour delay (at room temperature) between preparation of the complex and application to cells, expression was 28±10% (n=6) of the value obtained when the delay interval was only 15 minutes. In contrast, adenovirus alone retained its infectivity; expression after a 5 hour delay at room temperature was 104±7% (n=6) of the value after a 15 minute delay.

It was necessary to prepare the PLL-Ad complex in the absence of serum. When serum was present during complex formation, expression of the transgene in 9L gliosarcoma cells was reduced to 2.8±0.1% (n=3) of the value obtained after preparation in serum-free conditions.

Figure 8B:
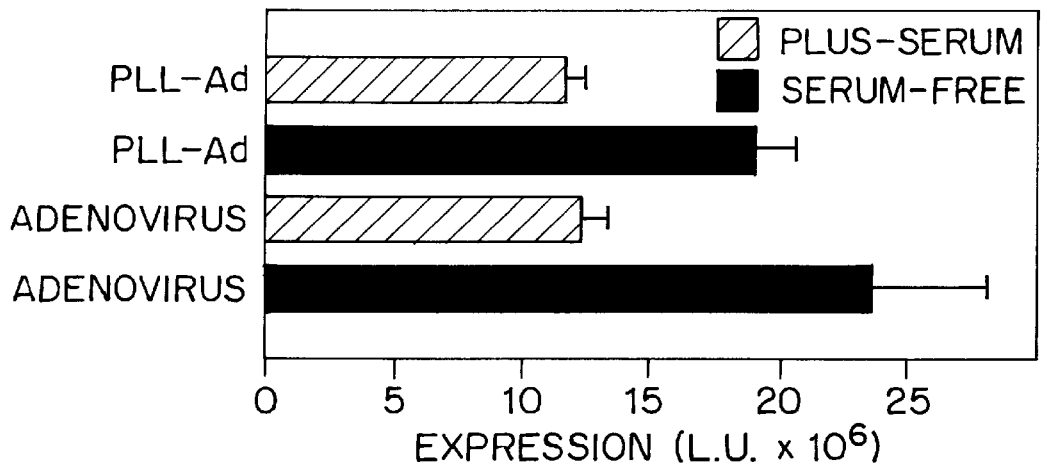
FIG. 8B is a graph demonstrating the effect of serum on gene transfer mediated by adenovirus alone or adenovirus complexed with PLL in COS cells.

Serum inhibits gene transfer by some cationic lipid/DNA complexes and by some nonviral vector preparations that contain PLL. To examine the effect of serum on the present complexes, COS-1 cells were used so that the effect of PLL-Ad could be compared to adenovirus alone. Adenovirus alone or PLL-Ad (prepared under serum-free conditions in Eagle's MEM at 5000 particles/cell, 250 PLL molecules/particle) was applied to COS-1 media containing 10% fetal calf serum (FIG. 8B, crosshatched bars). Vector was then removed, fresh media added, and β-galactosidase assayed 24 hours later.

FIG. 8B shows that PLL-Ad mediated gene transfer to COS-1 cells was decreased in the presence of serum, but the decrease was no greater than that observed with adenovirus alone. Similar results were obtained with 9L gliosarcoma cells. These data indicate that after the complex was formed, it could be used in either the presence or absence of serum.

Figure 8C:
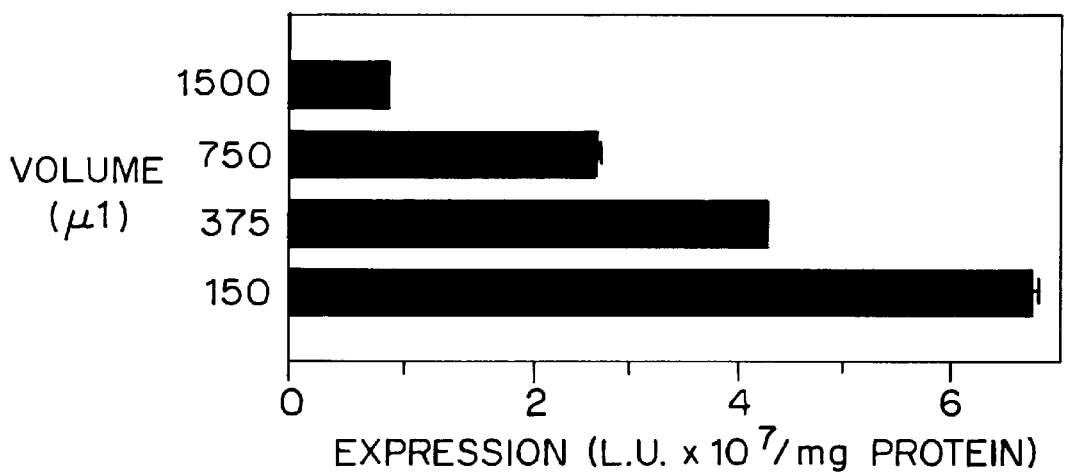
FIG. 8C is a graph demonstrating the effect of concentration of PLL-Ad on gene transfer to 9L gliosarcoma cells.

The effect of concentration of PLL-Ad on gene transfer to 9L gliosarcoma cells was evaluated. PLL-Ad (250 molecules/particle, 5000 particles Ad2/βGal-2/cell) was prepared and applied to cells in volumes indicated in FIG. 8C for two hours. β-galactosidase expression was measured 24 hours later. As the concentration of PLL-Ad increased (produced by decreasing the applied volume with a constant MOI) expression increased in 9L gliosarcoma cells (FIG. 8C).

Figure 8D:
FIG. 8D is a graph demonstrating the effect of growth state of 9L gliosarcoma cells on gene transfer mediated by adenovirus alone or adenovirus complexed with PLL.

The effect of time of culture of 9L gliosarcoma cells on adenovirus (FIG. 8D crosshatched bars) and PLL-Ad (solid bars) mediated gene transfer was examined. Vector was applied to confluent cells (seeded at $3 \times 10^5$ cells/cm$^2$) 48 hours after plating or to cells in log phase growth (seeded at $7.5 \times 10^4$ cells/cm$^2$) 18 hours after plating. β-galactosidase was measured 40 hours later. The enhancement produced by complexing adenovirus with PLL was not dependent on the time after seeding of 9L gliosarcoma cells (FIG. 8D). In confluent 9L gliosarcoma cells, expression with PLL-Ad was 32-fold greater than with adenovirus alone and with subconfluent cells in log phase growth expression was 29-fold greater.

The appearance of the PLL-Ad complex was examined by transmission electron microscopy. Adenovirus alone and PLL-Ad complexes at a suboptimal infection ratio (4 PLL molecules/particle of Ad2/βGal-2), an optimal ratio (250 PLL molecules/particle of Ad2/βGal-2), and another suboptimal ratio (10,000 PLL molecules/particle of Ad2/βGal-2) were used to infect 9L gliosarcoma cells as described in Example 1. FIGS. 6A–D show electron photomicrographs of adenovirus alone (6A) and PLL-Ad at a ratio of 4 (6B), 250 (6C) and 10,000 (6D) PLL molecules/particle of Ad2/βGal-2. As the number of PLL molecules/adenovirus particle increased, the adenovirus particles tended to clump together, although individual adenovirus particles were found even at the highest ratio. These observations suggest that PLL is linking the negative surface charge on the adenovirus particle to other particles and that excessive amounts of PLL produce aggregation which could decrease the efficiency of gene transfer, as shown in FIG. 5.

EXAMPLE 5

Effect of Fiber and Antiadenovirus Antibodies

In some cell types, adenovirus infection is mediated by binding of the adenovirus fiber protein to an unidentified receptor on the cell surface. (Persson et al. (1985) *J. Virol.* 54: 92.)

Figure 9A:
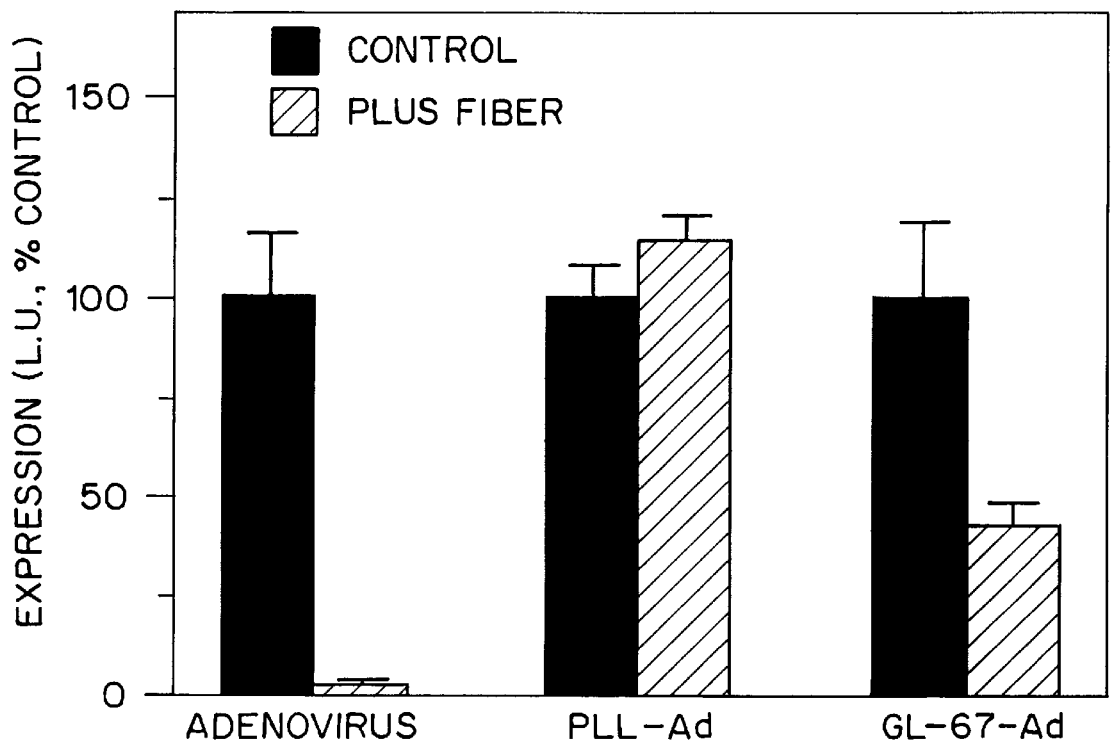
FIGS. 9A and B are graphs depicting the effect of fiber (9A) and antiadenovirus antibodies (9B) on gene transfer by adenovirus alone or complexed with PLL or complexed with a cationic lipid (GL-67).

In this example, the effect of fiber and antiadenovirus antibodies on gene transfer by adenovirus alone or by PLL-Ad was investigated. (Fiber protein 70 µg/ml) (FIG. 9A, crosshatched bar) or solution alone (FIG. 9 solid bar) was applied to primary cultures of rat hepatocytes in EMEM and 10 minutes later Ad2/βGal-2 alone, PLL-Ad (250 molecules PLL/particles, or GL-67-Ad ($2.2 \times 10^5$ molecules GL-67/particle) were added. Vector was removed 2 hours later and β-galactosidase was measured 20–24 hours later. n=4. Excess fiber inhibited gene transfer by adenovirus alone in primary hepatocytes, which are readily infected cells (FIG. 9A). However, fiber did not inhibit expression by PLL-Ad and only partially inhibited expression by GL-67-Ad (FIG. 9A).

The effect of adenovirus-neutralizing antibodies was also examined. Antifiber antibody (1:100 dilution, FIG. 9B, crosshatched bar), antihexon antibody (1:100 dilution, FIG. 9B, shaded bar), or solution alone (FIG. 9B, solid bar) was mixed with Ad2/βGal-2 or PLL-Ad at a ratio of either 25 or 250 PLL molecules/particle. The solution was incubated for 10 minutes at 25° C. and then applied to the cells. Vector was removed from the cells by rinsing 30 minutes later, and β-galactosidase activity was measured 20–24 hours later. Data are presented relative to expression in the absence of antibody. n=4.

Figure 9B:
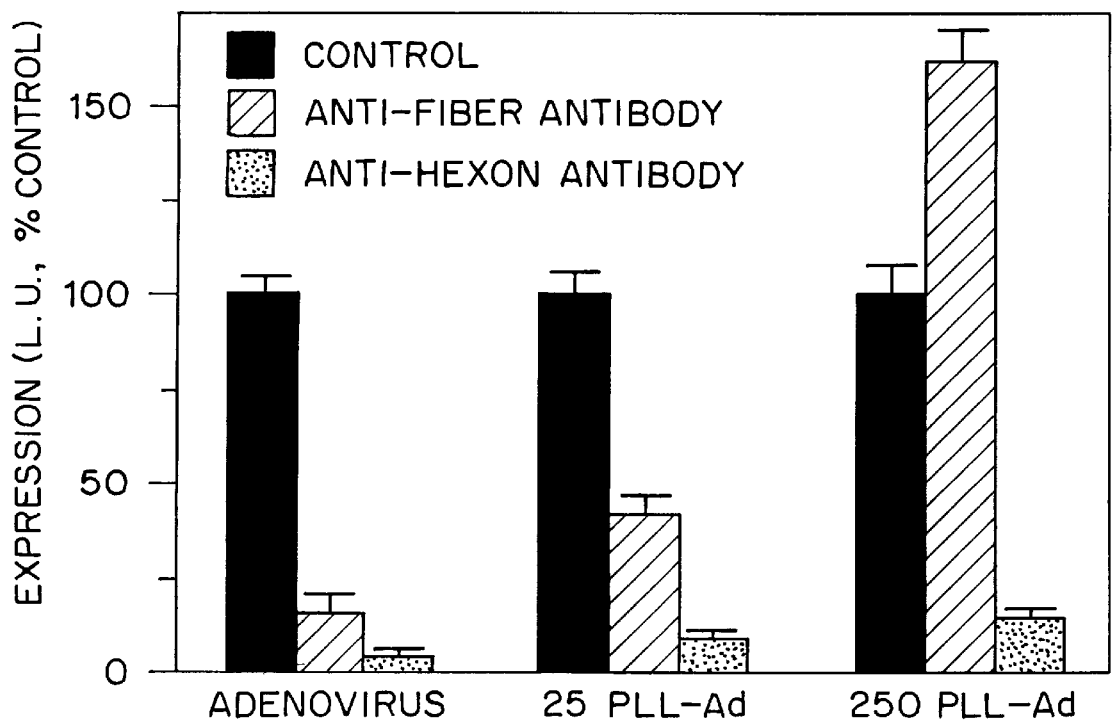

FIG. 9B shows that neutralizing antibodies directed against fiber did not interfere with expression by PLL-Ad when optimal PLL molecule/particle ratios were used. However, at a suboptimal ratio (25 PLL molecules/particle), anti-fiber antibody produced some inhibition of expression. In contrast, antihexon antibodies inhibited infection by both adenovirus and PLL-Ad (FIG. 9B). These data together with the adenovirus binding experiments, the effect of fiber, and the enhancement of gene transfer to poorly infected cells suggest that PLL allows adenovirus to bind to and then infect cells through pathways other than the fiber receptor-mediated pathway. However, the inhibition by antihexon antibody suggests that additional adenovirus-dependent steps subsequent to binding are required for infection.

Figure 10A:
FIGS. 10A–F are transmission electron micrographs of 9L gliosarcoma cells infected by Ad2/βGal-2 alone (10A, B), PLL-Ad at 250 molecules/particle (10C, D) and Lipofectamine-Ad at $6.9 \times 10^4$ DOSPA molecules/particle (10E, F).
Figure 10B:
Figure 10C:
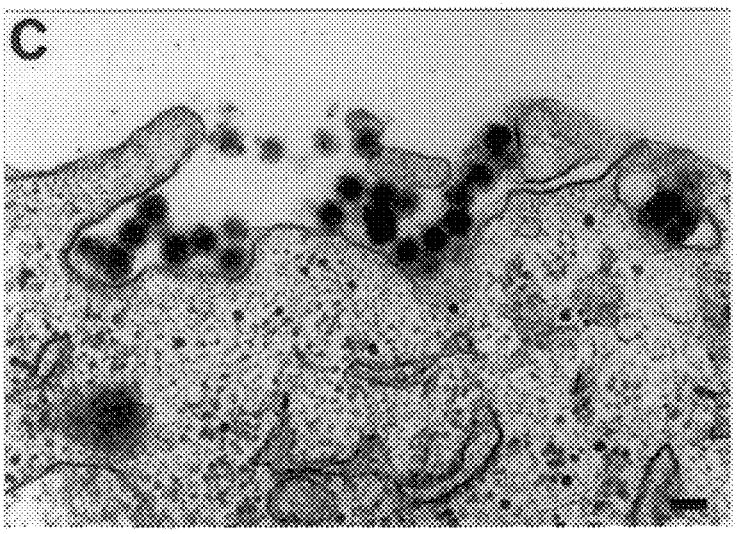
Figure 10D:
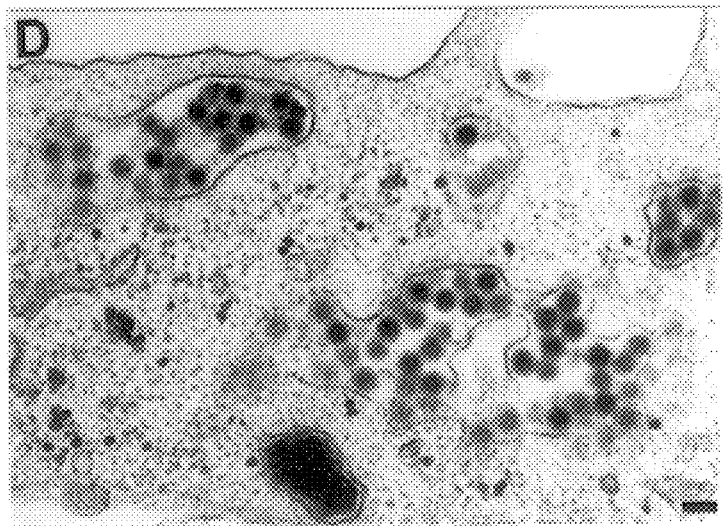
Figure 10E:
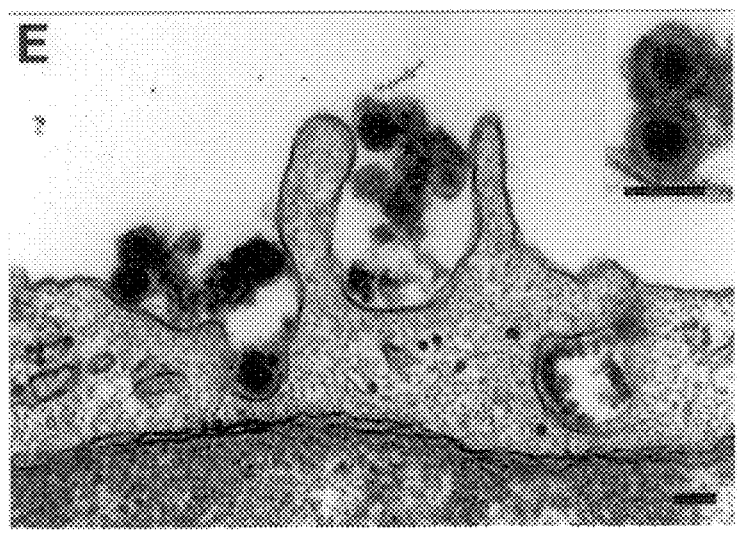
Figure 10F:
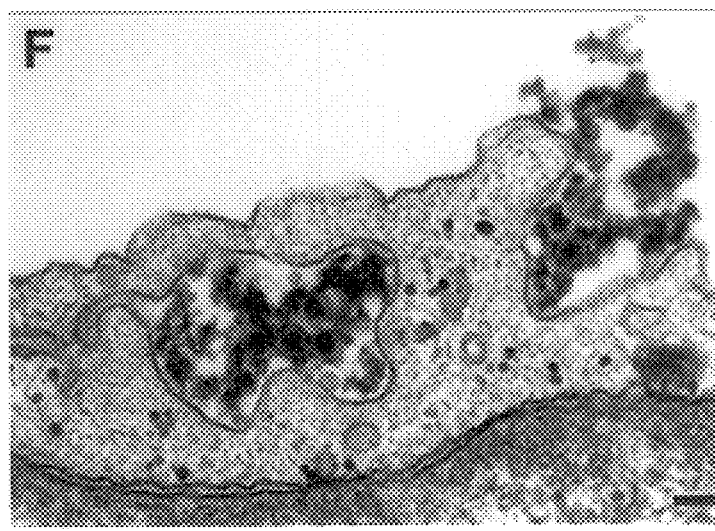

Transmission electron microscopy was used to further investigate the binding and uptake of the cationic molecule-adenovirus complex. Ad2/βGal-2 alone (FIGS. 10A, B), PLL-Ad (250 molecules/particle) (FIG. 10C, D) or Lipofectamine-Ad ($6.9 \times 10^4$ molecules/particle) (FIGS. 10E, F) were applied to 9L gliosarcoma cells. The inset in FIG. 10E shows higher magnification of lamellar structure of lipid surrounding adenovirus particles. Vector ($2 \times 10^6$ particles/cell) was applied for 15 minutes and then washed and prepared for microscopy as described in Example 1. All scale bars in FIGS. 10A–E indicate 100 nm.

9L gliosarcoma cells were used because they are poorly infected by adenovirus alone due to poor binding of virus. Further, a very large number of particles per cell were used in order to observe the vector-cell interaction. At high MOI's there were a substantial number of adenovirus particles in the cells, even in 9L gliosarcoma cells which show limited binding of adenovirus (FIG. 10A, B). The electron photomicrographs show that adenovirus was usually taken up into the cells as single particles or occasionally as a small (2 or 3) number of particles. In the cells treated with PLL-Ad (FIG. 10C, D) or Lipofectamine-Ad (FIG. 10E, F), there was a greatly increased number of adenovirus particles in the cells, consistent with the data shown in FIG. 1. It is also apparent that with the PLL-Ad and cationic lipid-Ad complexes, multiple adenovirus particles were present in the endosomes and that the endosomes were larger than those containing adenovirus alone. In addition, with cationic lipid-Ad complexes, a lamellar appearance of the lipid around and associated with the virus was sometimes observed. (inset in FIG. 10E).

EXAMPLE 6

Gene Transfer by Cationic Molecule-Adenovirus Complexes to Airway Epithelia

Figure 11A:
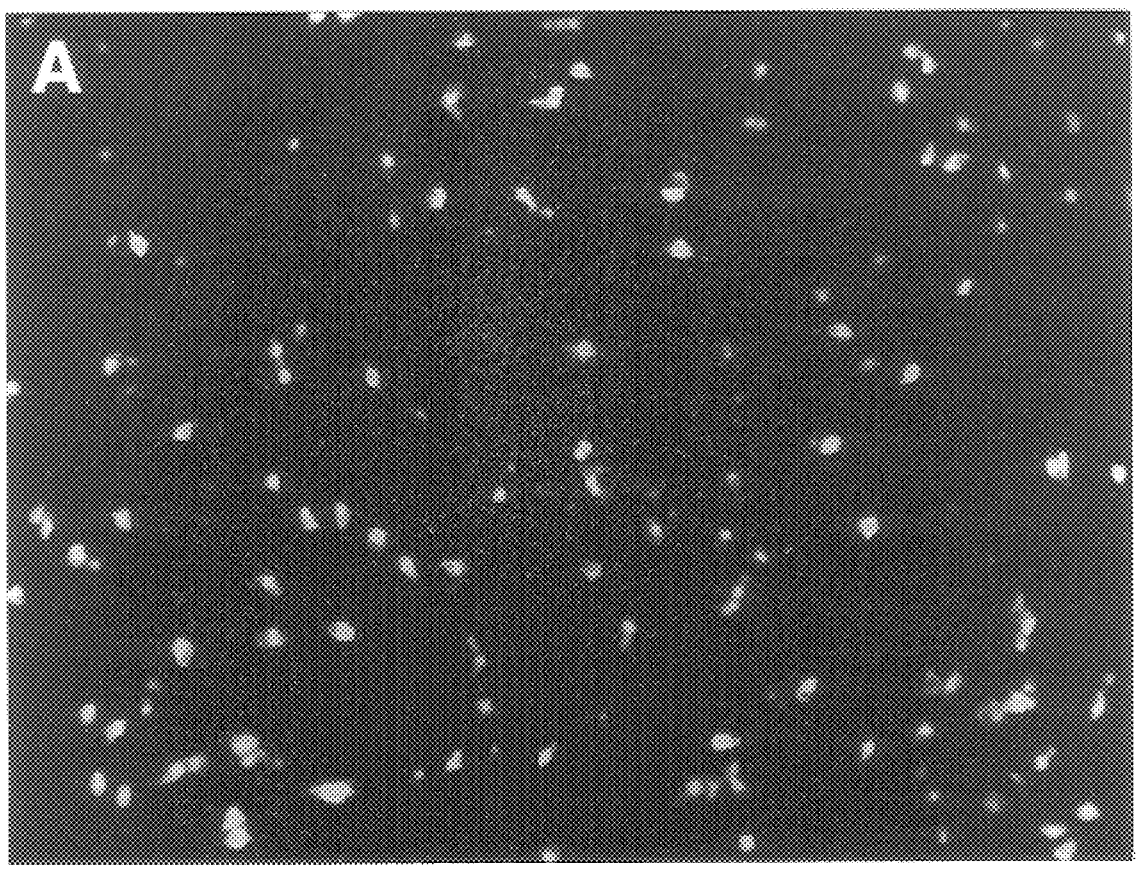
FIGS. 11A and B depict primary cultures of mature human airway epithelia infected by wild-type adenovirus alone (11A) or complexed with PLL and stained with antihexon antibody (11B).
Figure 11B:
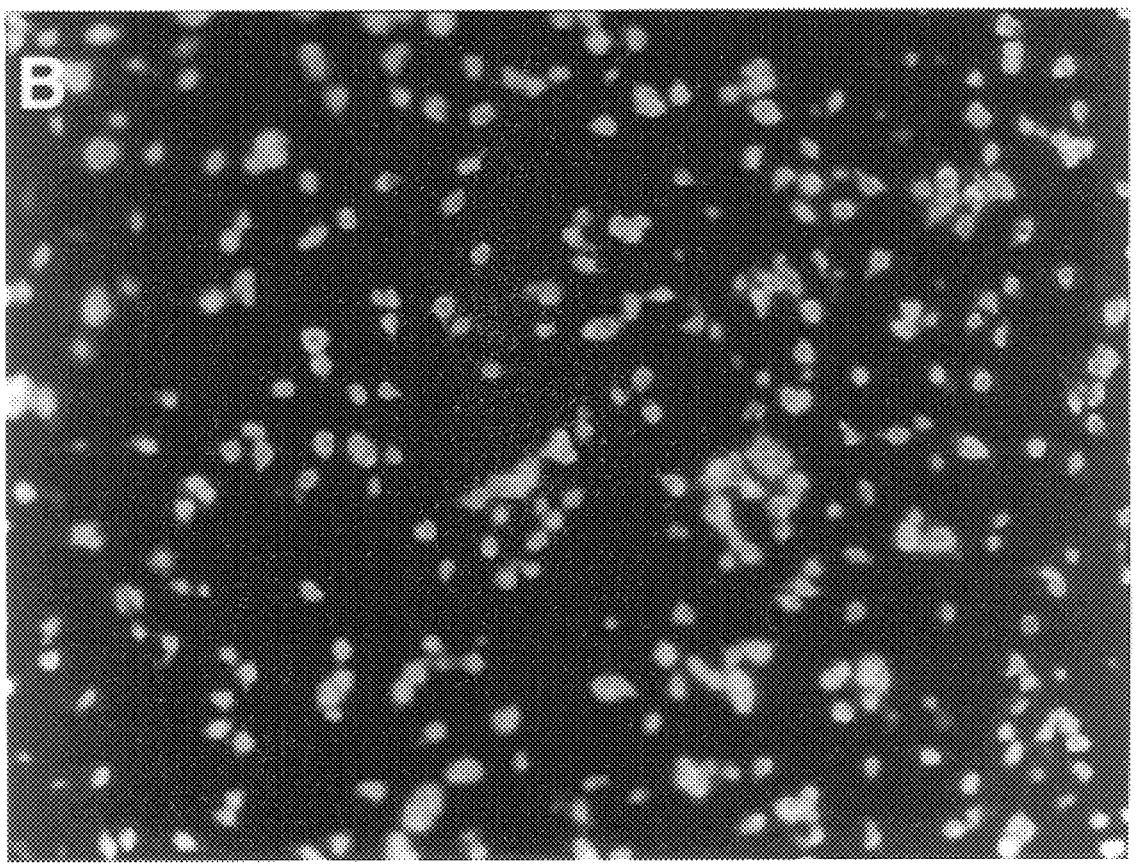

The effect of the complexes on gene transfer to airway epithelia was examined in vitro and in vivo. Primary cultures of human airway epithelia grown at the air-liquid interface differentiate into a respiratory epithelium that has a cilia-covered surface and many characteristics of native epithelium (Smith et al. (1996) *Cell* 85: 229.) Primary cultures of mature human airway epithelia were infected by wild-type adenovirus 2 alone (FIG. 11A) or with virus complexed with PLL (FIG. 11B). Epithelia were studied 21 days after they were seeded when they were confluent and differentiated. Ad2 or PLL-Ad (50 MOI, particle/I.U. ratio=12) was applied to apical surface of epithelia (approximately $5 \times 10^5$ cells per epithelium) for 30 minutes. Vector was then removed and the epithelium was rinsed to remove unattached virus. Thirty hours later epithelium was fixed and stained with antihexon antibody. FIG. 11 shows that more cells were infected with PLL-Ad than with adenovirus alone; there were 94±48 hexon-positive cells per low power field with adenovirus alone versus 797±115 with PLL-Ad (p=0.001, n=4).

Figure 12A:
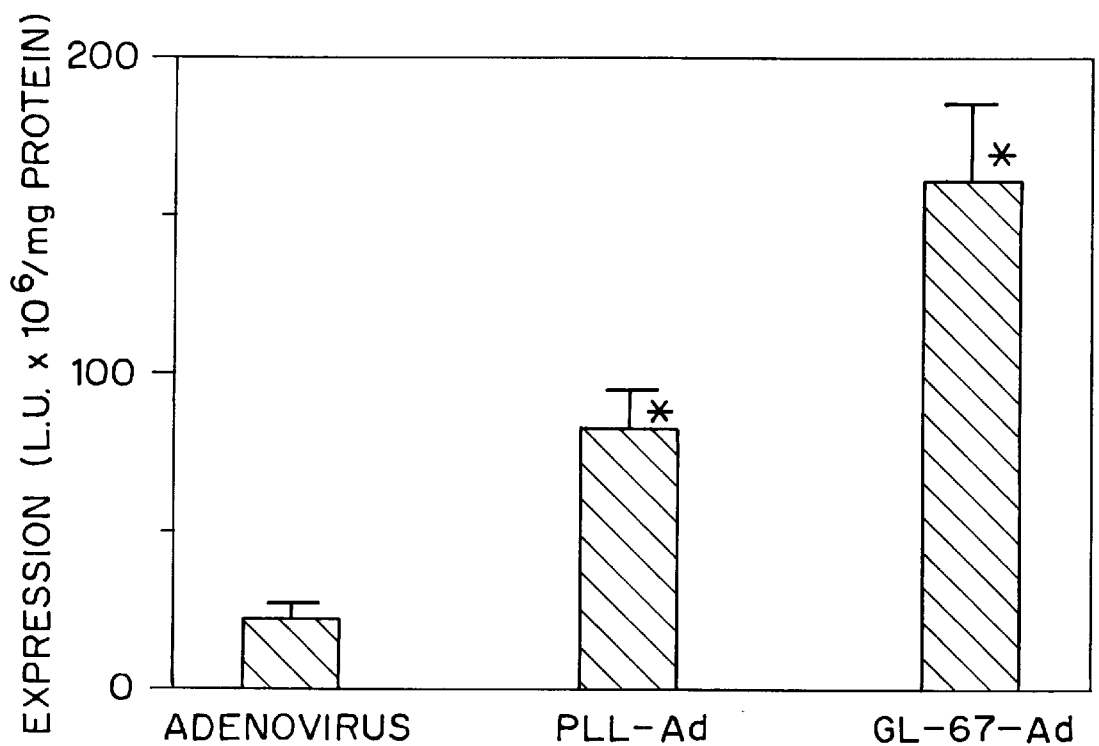
FIG. 12A depicts β-galactosidase activity in human airway epithelia infected by adenovirus alone, PLL-Ad, and GL-67-Ad.

The complexes were also applied to the mucosal surfaces of epithelial monolayers, after which β-galactosidase activity was measured. Ad2/βGal-2 alone, PLL-Ad (250 molecules/particle) or GL-67-Ad ($2.2 \times 10^5$ molecules/particle) was applied in 50 µl (approximately 20 MOI) to the apical surface. Vector was applied 12 days after cells were seeded and β-galactosidase activity was measured 4 days later. n=3. Asterisks in FIG. 12A indicate p<0.01 compared to adenovirus alone. FIG. 12A shows that epithelia treated with PLL-Ad or GL-67-Ad generated more β-galactosidase activity than those treated with adenovirus alone.

Figure 12B:
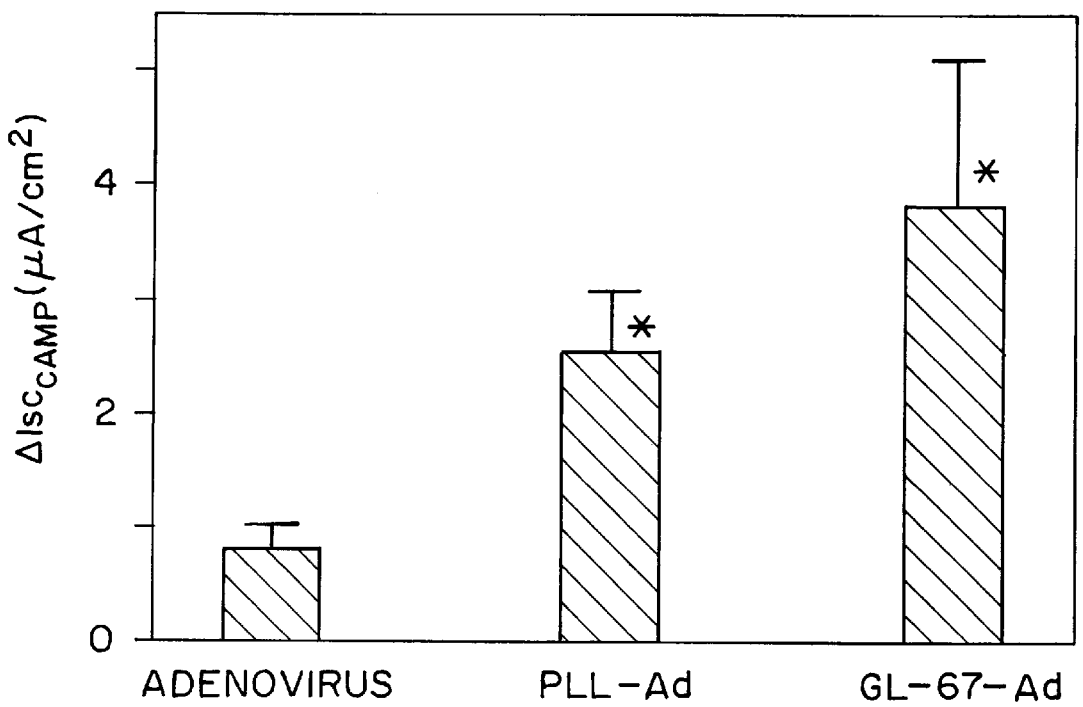
FIG. 12B depicts the change in transepithelial Cl⁻ current in response to cAMP agonists in CF airway epithelia infected by Ad2/CFTR-8, PLL-Ad2/CFTR-8 or GL-67-Ad2/CFTR-8.

Ad2/CFTR-8 was applied to CF airway epithelia 12 days after they were seeded. The change in short-circuit current in response to cAMP agonists was measured 5 days later. Results are shown in FIG. 12B; n=2, error bars indicate range.

FIG. 12 shows that application of adenovirus expressing CFTR to the apical surface of CF airway epithelia for 30 minutes had little effect on cAMP-stimulated Cl current to CF epithelia. However, treatment with PLL-Ad complexes restored a cAMP-stimulated Cl⁻ current to CF epithelia. These data demonstrate that the complexes are more efficient than adenovirus alone at CFTR gene transfer to mature human airway epithelia to produce a functional Cl⁻ channel.

Previous studies have administered adenoviral vectors encoding CFTR to the nasal epithelium of patients with CF and tested for correction of the electrophysiologic defect. Correction of the CF electrophysiologic abnormalities following application of Ad2/CFTR-1 to nasal epithelium that was injured during the application procedure has been reported by Zabner et al. (1993) *Cell* 75: 207. However, when adenoviral vector was applied to intact respiratory epithelium, only limited evidence of gene transfer was observed by Zabner et al. (1996) *J. Clin Invest*. 97: 1504. Hay et al. found evidence of partial electrophysiologic correction, and Knowles et al. (1995) *New Engl. J. Med*. 333: 823 found no evidence of correction. These data suggest that more efficient gene transfer to human ciliated respiratory epithelia in vivo would be valuable. Therefore the ability of PLL-Ad to correct the electrophysiologic defect in the nasal epithelium of CF mice (an animal model for the human disease) was tested.

Either Ad2/CFTR-8 alone or complexed with PLL (250 molecules PLL/particle) was applied to nasal epithelium of mice containing the ΔF508 mutation in the mouse CFTR gene. The ΔF508 mutation is the most common mutation in human CF patients, being present in about 70% of cases. Vector ($5 \times 10^7$ I.U./nostril) was applied to the nasal mucosa in 5 μl. Electrophysiologic measurements were obtained 2 days after vector administration. Data for wild-type (+/+) and CFTR-ΔF508 (ΔF/ΔF) mice that were not exposed to adenovirus are from Zeiher et al. (1995) *J. Clin. Invest*. 96: 2051 incorporated herein by reference. Asterisks in FIG. 13 indicate values different from the group treated with adenovirus alone (p<0.01). n=12 for adenovirus and 13 for PLL-Ad.

Figure 13A:
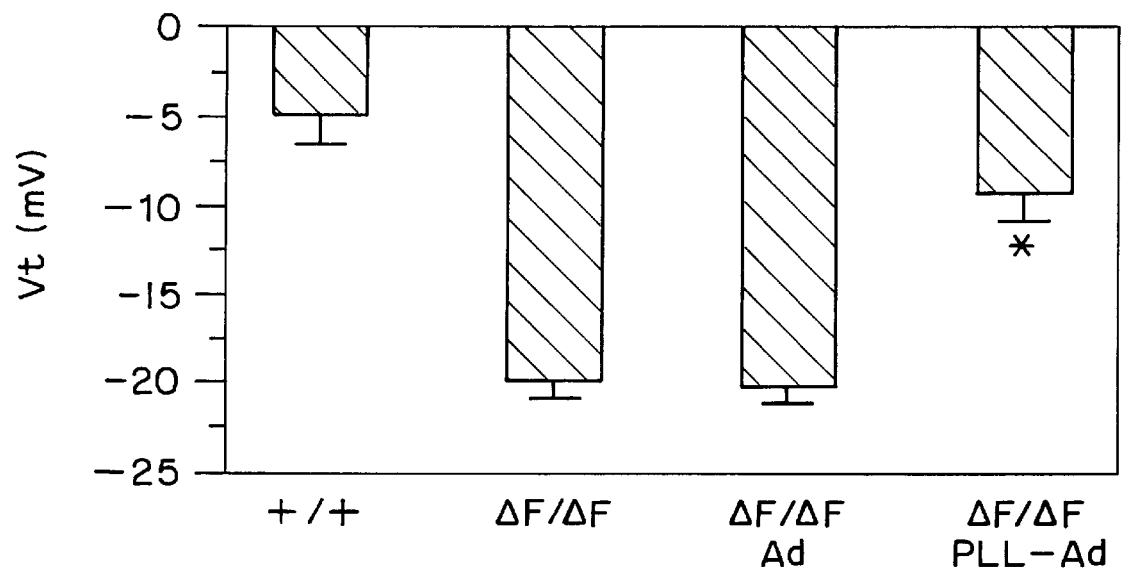
FIGS. 13A and B are graphs of basal voltage (A) and change in voltage produced by perfusion with a solution containing a low Cl⁻ concentration (B) and cAMP agonists in the presence of amiloride for CF mice bearing the ΔF508 mutation treated with Ad2/CFTR-8 alone or complexed with PLL.
Figure 13B:
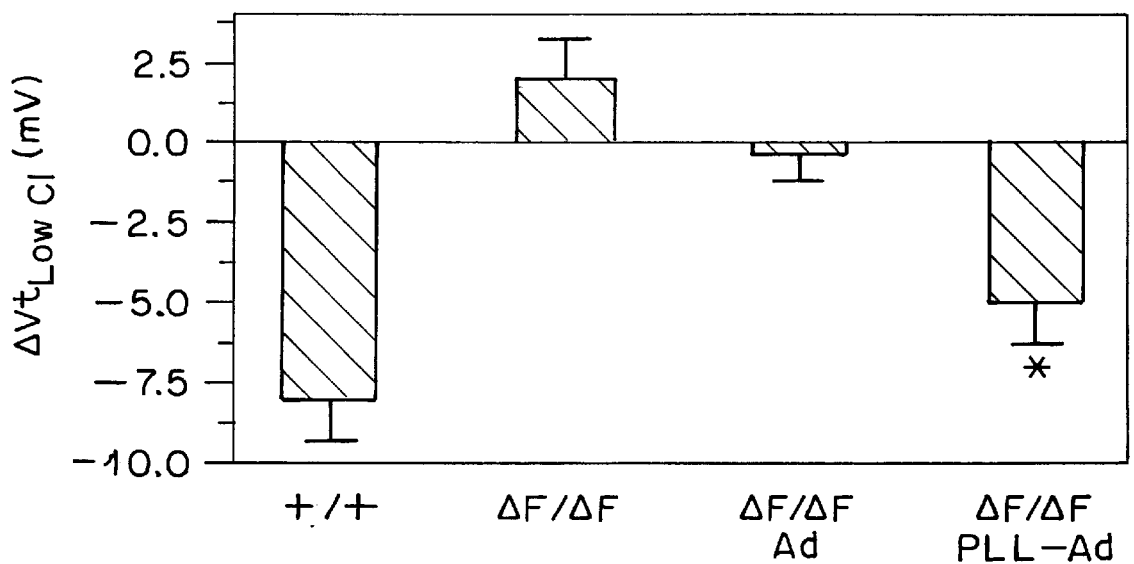

FIG. 13 shows that CF mice bearing the ΔF508 mutation have a basal voltage that was more electrically negative than wild-type mice, and the voltage failed to hyperpolarize in response to perfusion with a solution containing a low Cl⁻ concentration. Administration of Ad2/CFTR-8 alone failed to correct either of these defects (FIG. 13). However, after addition of PLL-Ad, both electrophysiologic properties were corrected into the normal range. These data indicate that functional CFTR Cl⁻ channels were restored in the nasal epithelium by application of PLL-Ad2/CFTR-8.

EXAMPLE 7

Figure 14A:
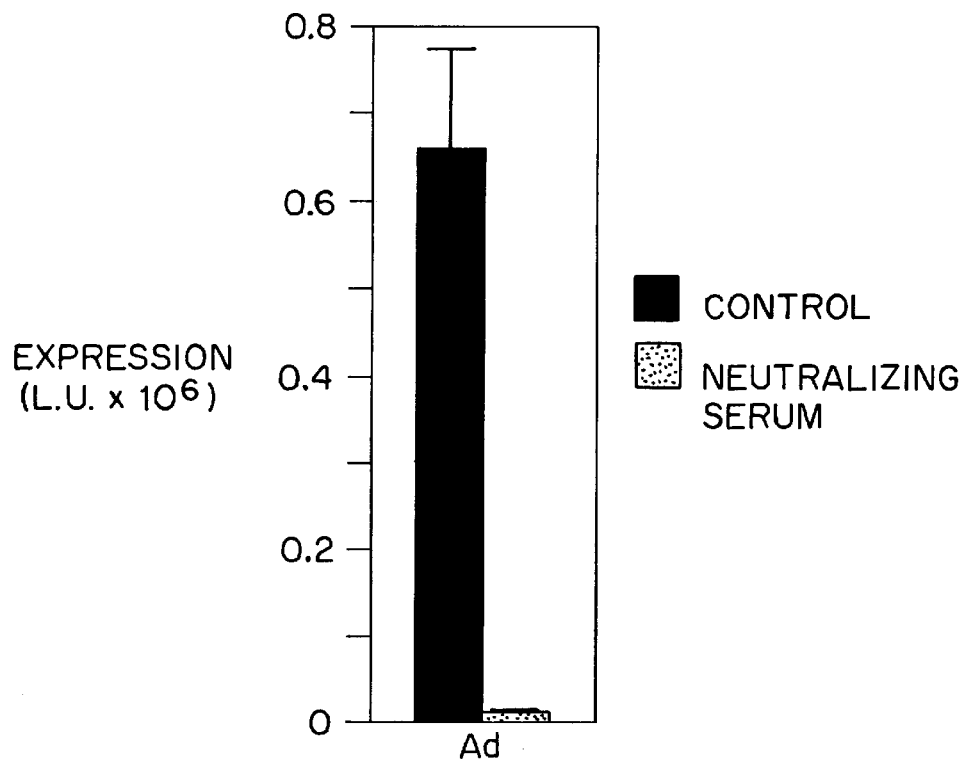
FIG. 14A depicts β-galactosidase activity in HeLa cells treated with Ad2/βGal-2 in the absence (solid bars) or presence (shaded bars) of serum containing neutralizing antibody.

Effect of Neutralizing Serum on Gene Transfer by Cationic Molecule-Adenovirus Complex HeLa cells were treated with Ad2/βGal-2 in the presence or absence of serum from a rat that had been immunized to adenovirus type 2. Expression of β-galactosidase was determined and is presented in FIG. 14A, in which solid bars indicate the absence of serum and shaded bars indicate the presence of serum. The results in FIG. 14A demonstrate that the serum contained neutralizing antibody.

Figure 14B:
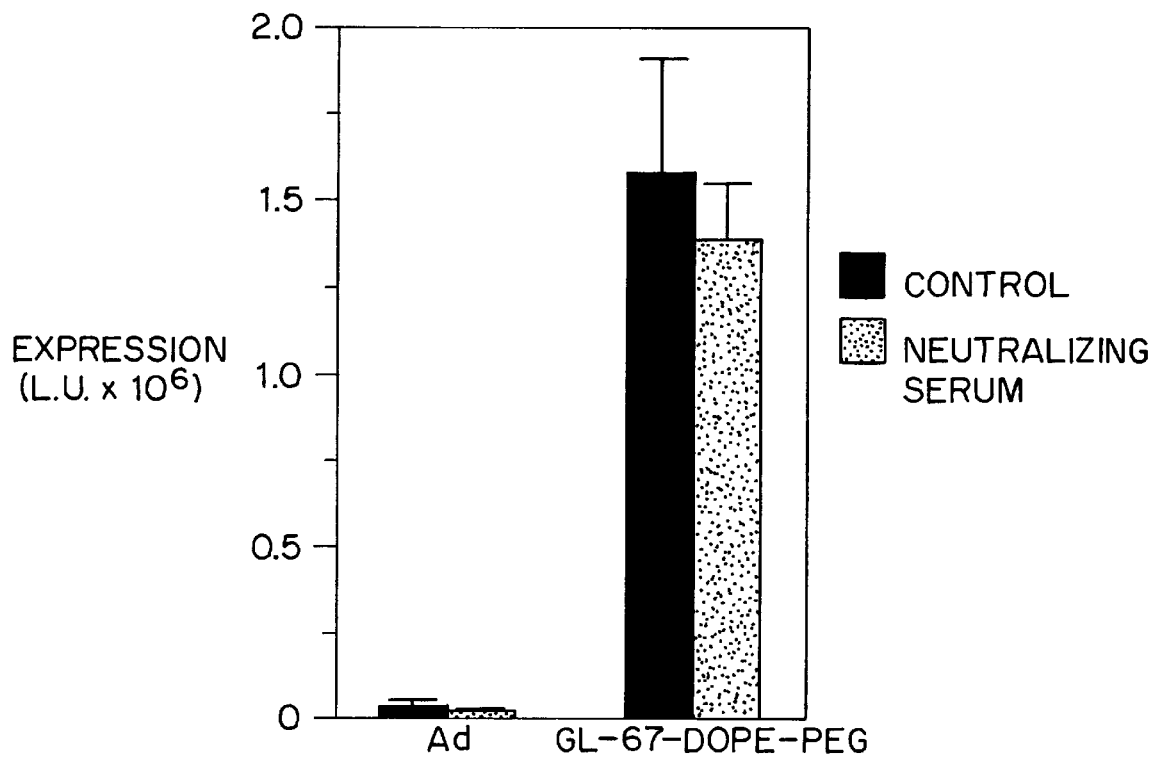
FIG. 14B depicts β-galactosidase activity in NIH-3T3 cells treated with Ad2/βGal-2 alone or complexed with GL-67/DOPE-PEG in the absence (solid bars) or presence (shaded bars) of serum containing neutralizing antibodies.

NIH-3T3 cells were treated with Ad2/βGal-2 alone or complexed with GL-67/DOPE-PEG in the absence (FIG. 14B, solid bars) or presence (FIG. 14B, shaded bars) of the neutralizing serum. Expression of β-galactosidase was determined and is presented in FIG. 14B. The data in FIG. 14B demonstrate that the complex was much more effective than adenovirus alone in delivering a transgene to NIH-3T3 cells, and that adenovirus complexed with a combination of GL-67/DOPE-PEG was protected from the effect of neutralizing antibody.

We claim:

1. A noncovalent complex comprising cationic lipids, or cationic polymers selected from the group consisting of poly-L-lysine, polyethyleneimine, DEAE-dextran, histone and cationic dendrimer, and adenoviral particles wherein said adenoviral particles comprise a transgene operably linked to an expression control sequence.

2. The noncovalent complex of claim 1 wherein said cationic lipids are selected from the group consisting of DC-Chol, GL-67, GL-53, DOSPA, DOGS, DOSPER, DOTAP, DOTMA, DMRIE, βAE-DMRIE, DDAB, LIPOFECTIN®, LIPOFECTAMINE™, LIPOFECTACE™, TRANSFECTAM®, Tfx™-50, and DMRIE-C™.

3. The noncovalent complex of claim 1 wherein said transgene encodes a cystic fibrosis transmembrane conductance regulator protein.

4. A composition comprising the noncovalent complex of claim 1 and a carrier.

5. A method of making a noncovalent complex comprising cationic lipids, or cationic polymers selected from the group consisting of poly-L-lysine, polyethyleneimine, DEAE-dextran, histone and cationic dendrimer, and adenoviral particles wherein said adenoviral particles comprise a transgene operably linked to an expression control sequence, said method comprising mixing said cationic lipids or cationic polymers with said adenoviral particles.

6. The method of claim 5 wherein said cationic lipids or polymers and said adenoviral particles are diluted in a pharmaceutically acceptable carrier.

7. The method of claim 5 wherein said cationic lipids are selected from the group consisting of DC-Chol, GL-67, GL-53, DOSPA, DOGS, DOSPER, DOTAP, DOTMA, DMRIE, βAE-DMRIE, DDAB, LIPOFECTIN®, LIPOFECTAMINE™, LIPOFECTACE™, TRANSFECTAM®, Tfx™-50 and DMRIE-C™.

8. The method of claim 5 wherein said transgene encodes a cystic fibrosis transmembrane conductance regulator protein.

9. A method for delivering a transgene to an airway epithelial cell comprising combining cationic lipids, or cationic polymers selected from the group consisting of poly-L-lysine, polyethyleneimine, DEAE-dextran, histone and cationic dendrimer, and adenoviral particles comprising said transgene operably linked to an expression control sequence to form a noncovalent complex, and introducing said complex into said airway epithelial cell.

10. The method of claim 9 wherein said complex is introduced into said airway epithelial cell by infection.

11. The method of claim 11 wherein said cationic lipids are selected from the group consisting of DC-Chol, GL-67, GL-53, DOSPA, DOGS, DOSPER, DOTAP, DOTMA, DMRIE, βAE-DMRIE DDAB, LIPOFECTIN®, LIPOFECTAMINE™, LIPOFECTACE™, TRANSFECTAM®, Tfx™-50 and DMRIE-C™.

12. The method of claim 9 wherein said transgene encodes cystic fibrosis transmembrane conductance regulator.

13. A method of providing cystic fibrosis transmembrane conductance regulator to airway epithelial cells of a cystic fibrosis patient comprising combining cationic lipids, or cationic polymers selected from the group consisting of poly-L-lysine, polyethyleneimine, DEAE-dextran histone and cationic dendrimer, with adenoviral particles containing a transgene encoding cystic fibrosis transmembrane conductance regulator, wherein said transgene is operably linked to an expression control sequence, to form a noncovalent complex, and administering said complex to the airway epithelial cells of said cystic fibrosis patient, in an amount and under conditions whereby said transgene is expressed and a functional chloride channel is produced in the airway epithelial cells of said patient.

14. The method of claim 13 wherein said complex is delivered to said airway epithelial cells by inhalation.

15. A method for delivering a transgene to a target cell in vitro comprising combining cationic lipids, or cationic polymers selected from the group consisting of poly-L-lysine, polyethyleneimine, DEAE-dextran, histone and cationic dendrimer, and adenoviral particles comprising said transgene operably linked to an expression control sequence to form a noncovalent complex, and introducing said complex into said target cell.

16. The method of claim 15 wherein said complex is introduced into said target cell by infection.

17. The method of claim 15 wherein said cationic lipids are selected from the group consisting of DC-Chol, GL-67, GL-53, DOSPA, DOGS, DOSPER, DOTAP, DOTMA, DMRIE, βAE-DMRIE, DDAB, LIPOFECTIN®, LIPOFECTAMINE™, LIPOFECTACE™, TRANSFECTAM™, Tfx™-50 and DMRIE-C™.

* * * * *

UNITED STATES PATENT AND TRADEMARK OFFICE
CERTIFICATE OF CORRECTION

PATENT NO. : 5,962,429
DATED : October 5, 1999
INVENTOR(S) : Welsh et al.

Page 1 of 1

It is certified that error appears in the above-identified patent and that said Letters Patent is hereby corrected as shown below:

Title Page:
Item [73] Assignee: "University of Iowa" should read -- University of Iowa Research Foundation --

CLAIMS

Column 22,
Line 67: "βAE-DMRIE DDAB" should read -- βAE-DMRIE, DDAB --

Column 24,
Line 17: TRANSFECTAM™" should read -- TRANSFECTAM® --

SPECIFICATION

Column 5,
Line 17: ammoniummethylsulfate" should read -- ammonium-methylsulfate --
Line 32: "N,N,N', N'-tetramethyl-" should read -- N,N,N',N'-tetrsmethyl- --

Column 13,
Line 9: "Fluorescently-labeled" should read -- Fluorescently labeled --
Line 15: "Uppsale," should read -- Uppsala, --
Line 3: "a" should read -- an --

Signed and Sealed this

Fourteenth Day of August, 2001

Attest:

NICHOLAS P. GODICI
Attesting Officer    Acting Director of the United States Patent and Trademark Office